(12) United States Patent
Kikuzawa

(10) Patent No.: US 11,597,132 B2
(45) Date of Patent: *Mar. 7, 2023

(54) FLEXIBLE TUBE PRODUCTION APPARATUS

(71) Applicant: PLA GIKEN CO., LTD., Osaka (JP)

(72) Inventor: Yoshiharu Kikuzawa, Osaka (JP)

(73) Assignee: PLA GIKEN CO., LTD., Osaka (JP)

( * ) Notice: Subject to any disclaimer, the term of this patent is extended or adjusted under 35 U.S.C. 154(b) by 685 days.

This patent is subject to a terminal disclaimer.

(21) Appl. No.: 16/525,170

(22) Filed: Jul. 29, 2019

(65) Prior Publication Data

US 2019/0351600 A1 Nov. 21, 2019

Related U.S. Application Data

(63) Continuation of application No. PCT/JP2019/010254, filed on Mar. 13, 2019.

(30) Foreign Application Priority Data

Mar. 13, 2018 (JP) .................................. 2018-045752
Mar. 12, 2019 (JP) .................................. 2019-044748

(51) Int. Cl.
*B29C 48/34* (2019.01)
*B29C 48/10* (2019.01)
(Continued)

(52) U.S. Cl.
CPC ............. *B29C 48/34* (2019.02); *B29C 48/10* (2019.02); *B29C 48/154* (2019.02); *B29C 48/155* (2019.02); *B29L 2031/7542* (2013.01)

(58) Field of Classification Search
CPC ....... B29C 48/09; B29C 48/10; B29C 48/151; B29C 48/154; B29C 48/155;
(Continued)

(56) References Cited

U.S. PATENT DOCUMENTS 5,059,375 A 10/1991 Lindsay
10,350,808 B2 * 7/2019 Kikuzawa ............. B29C 48/338
(Continued)

FOREIGN PATENT DOCUMENTS

JP 59-71841 A 4/1984
JP 2000-326384 A 11/2000
(Continued)

OTHER PUBLICATIONS

European Search Report for corresponding Application No. 19742118.3, dated Jan. 29, 2020.
(Continued)

*Primary Examiner* — Xiao S Zhao
*Assistant Examiner* — Joseph S Leyson
(74) *Attorney, Agent, or Firm* — Renner, Otto, Boisselle & Sklar, LLP

(57) ABSTRACT

A flexible tube production apparatus includes a die composed of: a cylindrical inner die having an outer face in which a groove is formed; a tubular member that is housed inside the inner die, and has a through-hole that allows a blade wire to be inserted from one end to the other end thereof; and an outer die that surrounds the inner die such that a predetermined gap is generated between itself and the outer face of the inner die, and has an extrusion hole that extrudes the resins having been supplied to the gap, onto the outer face of the blade wire that is fed from the other end of the tubular member. A resin supply portion supplies a first resin and a second resin to the die while the motor rotates the inner die about a center axis.

2 Claims, 16 Drawing Sheets

(51) Int. Cl.
*B29C 48/154* (2019.01)
*B29C 48/155* (2019.01)
*B29L 31/00* (2006.01)

(58) Field of Classification Search
CPC . B29C 48/2528; B29C 48/2552; B29C 48/33; B29C 48/34; B29C 48/49; B29L 2031/7542
See application file for complete search history.

(56) References Cited

U.S. PATENT DOCUMENTS

| | | | |
|---|---|---|---|
| 2005/0003034 A1* | 1/2005 | Watanabe | B29C 48/15 425/467 |
| 2005/0009178 A1 | 1/2005 | Yost et al. | |
| 2005/0260407 A1 | 11/2005 | Anand et al. | |
| 2007/0243282 A1* | 10/2007 | Kikusawa | B29C 48/06 425/461 |
| 2012/0187595 A1 | 7/2012 | Ohigawa et al. | |
| 2017/0368733 A1 | 12/2017 | Kikuzawa | |

FOREIGN PATENT DOCUMENTS

| | | |
|---|---|---|
| JP | 2004-535950 A | 12/2004 |
| JP | 2012-153002 A | 8/2012 |
| JP | 6144862 B1 | 5/2017 |
| WO | 02/085440 | 10/2002 |

OTHER PUBLICATIONS

International Search Report for parent Application No. PCT/JP2019/010254, dated May 21, 2019.
Written Opinion for parent Application No. PCT/JP2019/010254, dated May 21, 2019.

* cited by examiner

FLEXIBLE TUBE PRODUCTION APPARATUS

CROSS-REFERENCE TO RELATED APPLICATION

This application is a Continuation of International Application No. PCT/JP2019/010254, filed on Mar. 13, 2019, which in turn claims the benefits of Japanese Application No. 2018-045752 filed on Mar. 13, 2018 and Japanese Application No. 2019-044748 filed on Mar. 12, 2019, the disclosures of which Applications are incorporated by reference herein.

BACKGROUND

Field

The present invention relates to a flexible tube production apparatus for producing, through extrusion molding, a flexible tube in which the outer face of a blade is covered with a resin.

Description of the Related Art

In medical institutions, in order to inject a drug solution, a contrast medium, or the like to a predetermined site in the living body of a patient, or in order to take out body fluid or the like from the living body, a tubular medical instrument called a catheter is used. Since the catheter is inserted into the living body through a winding blood vessel or the like, an insertion tip portion of the catheter is required to have flexibility so as to easily bend along the winding portion of the blood vessel or the like, without damaging the blood vessel or the like. Meanwhile, a portion, of the catheter, that is not inserted into the living body is required to have moderate rigidity so as to facilitate operation of the catheter. Thus, various types of apparatuses for producing catheters, whose hardness is varied stepwise along the length direction thereof such that the tip portion is soft while the opposed-side portion is hard, have been proposed.

For example, Japanese Patent No. 6144862 discloses a flexible tube production apparatus provided with a mixing valve capable of changing the mixing ratio of a first resin to a second resin. Japanese Patent No. 6144862 describes a structure in which a resin mixing portion for mixing the first resin and the second resin is provided at a junction of a flow path through which the first resin is supplied from the mixing valve to a die and a flow path through which the second resin is supplied from the mixing valve to the die, or to the die side relative to the junction, thereby inhibiting uneven mixture of the first resin and the second resin.

In a case where a resin layer covering a flexible tube is formed from a mixture of two kinds of resins and the property of the resin layer is varied along the length direction of the flexible tube by changing the mixing ratio of the two kinds of resins, it is preferable to evenly mix the two kinds of resins as described in Japanese Patent No. 6144862 so as to make the variation in the property of the resin layer smooth. In order to change the mixing ratio of the two kinds of resins with good response or in order to freely adjust the length of a part where the mixing ratio of the two kinds of resins changes, it is preferable that the flow path for the resin from the mixing valve to the die is short. In the flexible tube production apparatus disclosed in Japanese Patent No. 6144862, since the resin mixing portion is provided, the flow path from the mixing valve to the die is likely to be long, and therefore, there is room for improvement in the structure of the resin mixing portion. Meanwhile, dimensional stability, i.e., uniform outer diameter, is a necessary requirement for a flexible tube used as a catheter or a tube for an endoscope. As described above, when the resin layer of the flexible tube is molded while changing the mixing ratio of the two kinds of resins, there are various requirements to be considered.

SUMMARY

Therefore, an object of the present invention is to provide an apparatus suitable for producing a flexible tube in which the mixing ratio of two kinds of resins that form a resin layer is continuously changed.

A flexible tube production apparatus according to an embodiment of the present invention includes: a die that extrudes a resin onto a surface of a blade wire; a resin supply portion capable of supplying, to the die, a first resin and a second resin different from the first resin; and a motor. The die includes: a cylindrical inner die having an outer face in which a groove is formed; a tubular member housed inside the inner die, the tubular member having a through-hole that allows the blade wire to be inserted from one end to the other end of the tubular member; and an outer die surrounding the inner die such that a predetermined gap is generated between the outer die and the outer face of the inner die, the outer die having an extrusion hole that extrudes the resins having been supplied to the gap, onto the outer face of the blade wire that is fed from the other end of the tubular member. The outer die, the inner die, and the tubular member are arranged such that the center axes thereof are coaxial with each other. The tubular member is fixed. The resin supply portion supplies the first resin and the second resin to the die while the motor rotates the inner die about the center axis.

A flexible tube production apparatus according to another embodiment of the present invention includes: a die that extrudes a resin onto a surface of a blade wire; a resin supply portion capable of supplying, to the die, a first resin and a second resin different from the first resin; and a motor. The die includes: a tubular member having a through-hole that allows the blade wire to pass through, the tubular member having a tubular first member and an annular second member, the first member having a first open end into which the blade wire is inserted, the second member being connected to the first member, having a second open end from which the blade wire is fed, and having an outermost diameter greater than an outer diameter of the first member; a cylindrical inner die surrounding the first member of the tubular member, and having an outer face in which a groove is formed; and an outer die surrounding the inner die and the second member such that a predetermined gap is generated between the outer die and the outer face of the inner die and between the outer die and the outer face of the second member, the outer die having an extrusion hole that extrudes the resin supplied to each gap, onto the outer face of the blade wire that is fed from the second open end. The outer die, the inner die, and the tubular member are arranged such that center axes thereof are coaxial with each other. The tubular member is fixed. The resin supply portion supplies the first resin and the second resin to the die while the motor rotates the inner die about the center axis.

According to the present invention, it is possible to provide an apparatus suitable for producing a flexible tube in which the mixing ratio of two kinds of resins that form a resin layer is continuously changed.

DETAILED DESCRIPTION

Hereinafter, embodiments of the present invention are described. In the following description, an example is described in which the present invention is applied to a flexible tube production apparatus having a configuration in which a blade (net tube) is provided on the outer face of an inner layer tube as a resin layer, and furthermore, the blade is covered with an outer layer tube as a resin layer. A catheter shaft is an example of the flexible tube. However, the catheter shaft is merely an example of the flexible tube, and the present invention is also applicable to a production apparatus for a flexible tube having another usage such as a flexible tube used for an endoscope.

First Embodiment

Configuration of Flexible Tube Production Apparatus

Figure 1:
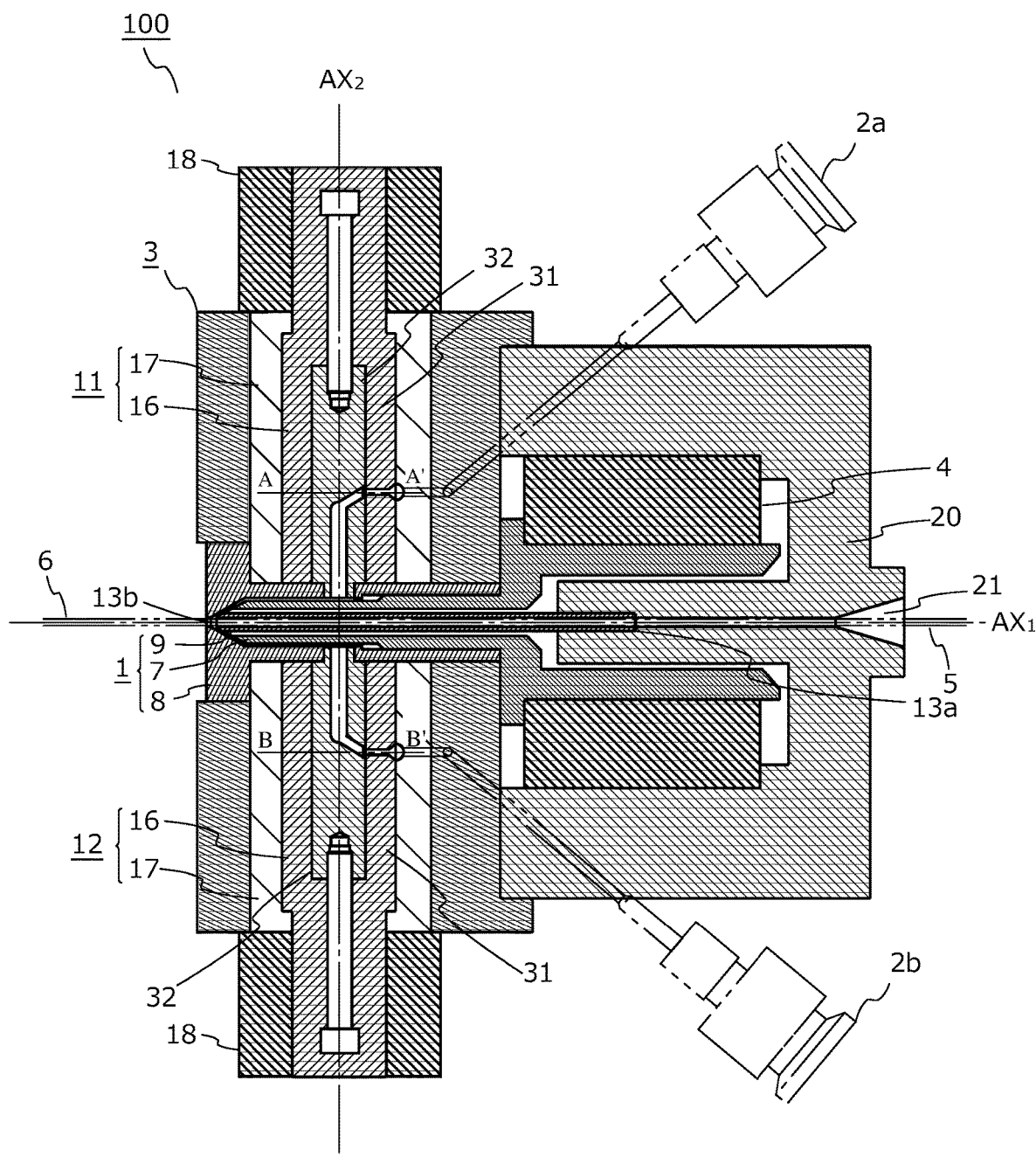
FIG. 1 is a horizontal cross sectional view showing a schematic configuration of a flexible tube production apparatus according to a first embodiment.
Figure 2:
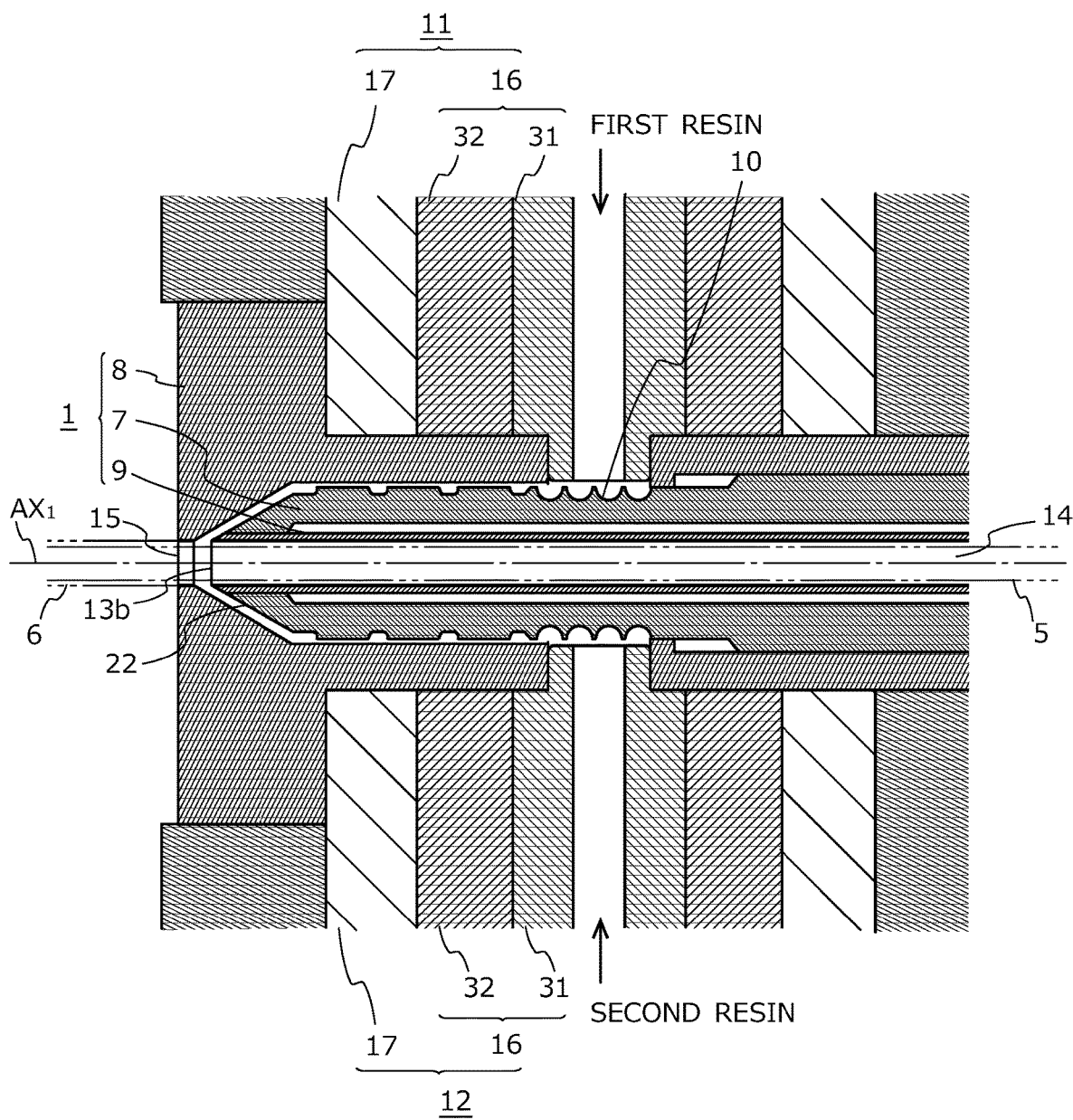
FIG. 2 is an enlarged view of a tip portion of a die shown in FIG. 1.

FIG. 1 is a horizontal cross-sectional view showing the schematic configuration of a flexible tube production apparatus according to the first embodiment. FIG. 2 is an enlarged view of a tip portion of a die shown in FIG. 1.

The flexible tube production apparatus 100 includes a die 1, a first extruder 2a, a second extruder 2b, a mixing valve 3, and a motor 4. The flexible tube production apparatus 100 is fixed to a predetermined mounting base or the like with a pedestal interposed therebetween. Although not shown, a supply device for supplying a blade wire 5, a haul-off device for hauling off a flexible tube 6 that has been extrusion-molded, and the like are provided as appropriate at the upstream side and the downstream side of the flexible tube production apparatus 100. The blade wire 5 is conveyed from the rear side to the front side of the flexible tube production apparatus 100 in the leftward direction shown in FIG. 1 and FIG. 2. The blade wire 5 is obtained by providing a blade (net tube) on an inner layer tube, and inserting a core wire (guide wire) into a hollow part of the inner layer tube. The flexible tube 6 is obtained by providing an outer layer tube at the surface of the blade wire 5. A catheter shaft is obtained by extracting the core wire of the blade wire after molding of the outer layer tube.

The die 1 is a die for extruding a resin onto the outer face of the blade wire 5, and includes an inner die 7, an outer die 8, and a tubular member 9. The inner die 7, the outer die 8, and the tubular member 9 are arranged such that the center axes thereof are coaxial with each other. Hereinafter, the center axis common to the inner die 7, the outer die 8, and the tubular member 9 is referred to as an axis $AX_1$.

The inner die 7 is a member having a hollow cylindrical shape, and has a forward-tapered portion at a tip end thereof. At an outer face of the inner die 7, a helically extending groove 10 is formed. The groove 10 is provided for kneading the resin supplied to a resin flow path provided between the inner die 7 and the outer die 8. The inner die 7 is supported by the outer die 8 so as to be rotatable about the axis $AX_1$, and is connected to the motor 4 described later.

The outer die 8 is a member having a hollow part corresponding to the outer shape of the inner die 7. The inner die 7 is housed in the hollow part of the outer die 8, and a predetermined gap is formed between the outer face of the inner die 7 and the inner face of the outer die 8. This gap serves as a flow path for the resin extruded onto the outer face of the blade wire 5. An extrusion hole 15 for extruding the resin supplied to the gap between the outer face of the inner die 7 and the inner face of the outer die 8 while feeding the supplied blade wire 5 frontward, is provided at a front end of the outer die 8.

The tubular member 9 is a tubular member having a through-hole 14 that allows the blade wire 5 to be inserted from a rear end 13a to a front end 13b. The tubular member 9 is housed inside the inner die 7. A portion, of the tubular member 9, within a predetermined range from the rear end 13a is fixed to a housing 20, whereby rotation of the tubular member 9 about the axis $AX_1$ is regulated. A contact part between the tubular member 9 and the inner die 7 is a slidable face.

The housing 20, to which the tubular member 9 is fixed, has a through-hole 21 that is coaxial with the axis $AX_1$ and is continuous to the through-hole 14 of the tubular member 9. The through-hole 21 of the housing 20, the through-hole 14 of the tubular member 9, and the extrusion hole 15 of the outer die 8 form a path that allows the blade wire 5 to pass through.

Each of the first extruder 2a and the second extruder 2b is a screw extruder, for example, and melts pellets of the resin and extrudes the melted resin at a constant speed from an outlet provided at a tip end thereof. The first extruder 2a and the second extruder 2b are supplied with a first resin and a second resin, respectively. The first resin and the second resin are different in at least one of properties such as hardness, tensile strength, elongation, elastic modulus in tension, and bending strength. The melted resins respectively ejected from the first extruder 2a and the second extruder 2b are supplied to the mixing valve 3 described later, are adjusted to a predetermined mixing ratio by the mixing valve 3, and are supplied to the die 1.

The mixing valve 3 is a member capable of changing the mixing ratio of the two kinds of resins extruded from the first extruder 2a and the second extruder 2b. The mixing valve 3 according to the present embodiment is composed of a first valve 11 and a second valve 12 which are separated bodies. Each of the first valve 11 and the second valve 12 includes: a columnar valve body 16 that is rotatable about an axis $AX_2$; and a valve case 17 in which the valve body 16 is rotatably housed. In the examples shown in FIG. 1 and FIG. 2, the first valve 11 and the second valve 12 are arranged such that the center axes thereof are coaxial with each other. However, arrangement of the first valve 11 and the second valve 12 is not limited thereto.

The valve body 16 is composed of a hollow first cylinder 31, and a second cylinder 32 that is housed in the first cylinder 31 and fixed to the first cylinder 31. Details of the first cylinder 31 and the second cylinder 32 will be described later. A space having a columnar shape that is substantially the same as the outer shape of the valve body 16 is provided in the valve case 17, and the valve body 16 is housed in this space. While being housed in the valve case 17, the valve body 16 is rotatably supported about the axis $AX_2$, with the outer peripheral surface of the valve body 16 sliding relative to the inner peripheral surface of the valve case 17. The valve body 16 is connected to a drive mechanism 18 such as a motor. The drive mechanism 18 rotates the valve body 16 about the axis $AX_2$ in accordance with control of a control device (not shown). The first valve 11 and the second valve 12 can change the mixing ratio of the first resin to the second resin to be supplied to the die 1, depending on the rotational positions of the valve bodies 16 thereof. Details of the mixing valve 3 will be described later.

The first extruder 2a, the second extruder 2b, and the mixing valve 3 described above form a resin supply portion capable of supplying the first resin and the second resin to the die 1.

The motor 4 is connected to the inner die 7 of the die 1, and rotates the inner die 7 about the axis $AX_1$ in accordance with control of a control device (not shown).

During extrusion molding of the flexible tube 6, the blade wire 5 inserted from the through-hole 21 of the housing 20 passes the through-hole 14 of the tubular member 9, and is pulled out from the extrusion hole 15 of the outer die 8 to the front of the flexible tube production apparatus 100, as shown by a two-dot chain line in FIG. 1 and FIG. 2. The blade wire 5 pulled out from the extrusion hole 15 of the outer die 8 is hauled by a haul-off device (not shown) to be continuously conveyed in the leftward direction in FIG. 1 and FIG. 2. With the blade wire 5 being conveyed, the first resin ejected from the first extruder 2a and/or the second resin ejected from the second extruder 2b are supplied to the resin flow path of the die 1 via the mixing valve 3. Then, the resins are extruded onto the outer face of the blade wire 5 passing through the extrusion hole 15, whereby the blade wire 5 is covered with the resin layer (outer layer tube), resulting in the flexible tube 6.

In the flexible tube production apparatus 100 according to the present invention, supply of the resins to the die 1 is performed while the inner die 7 is being rotated about the axis $AX_1$ by the motor 4. Since the helical groove 10 is formed at the outer face of the inner die 7, the resins supplied to the resin flow path between the outer face of the inner die 7 and the inner face of the outer die 8 are extruded toward the extrusion hole 15 while being kneaded in accordance with rotation of the inner die 7 about the axis $AX_1$. Therefore, the two kinds of resins supplied to the die 1 are actively uniformized through the path from the supply points (the outlets of the first valve 11 and the second valve 12) to the extrusion hole 15. When a flexible tube in which the property (e.g., hardness) of a resin layer is gradually changed along the longitudinal direction is formed by extrusion molding, the mixing ratio of two kinds of resins needs to be changed along with the extrusion. In the flexible tube production apparatus 100 according to the present invention, since rotation of the inner die 7 causes the two kinds of resins to be kneaded in the resin flow path, uneven mixture of the two kinds of resins is hindered, and the property of the resin layer can be continuously and smoothly changed along the longitudinal direction of the flexible tube 6.

Furthermore, both extrusion of the resins and kneading of the resins can be performed in the die 1. Therefore, the length and volume of the flow path from the mixing position of the two kinds of resins (in this embodiment, the most upstream part of the resin flow path provided in the die 1) to the extrusion hole can be reduced as compared with a case where a mixing screw or the like for resin kneading is provided in addition to the die for resin extrusion. Therefore, it is possible to improve a response from when the mixing ratio of the two kinds of resins is switched in the mixing valve 3 to when the mixing ratio of the resins extruded from the extrusion hole 15 is actually changed.

The outer layer of the blade wire 5 is formed of a braided layer or a wound layer of a metal wire or an element wire such as resin fiber. As for the element wire, a fine element wire having a diameter less than 1 mm is used. In a general extrusion molding apparatus for a flexible tube, in order to prevent the outer layer of the blade wire 5 from being damaged, the inner die through which the blade wire 5 is inserted is used in its fixed state. In the flexible tube production apparatus 100 according to the present invention, in order to rotate the inner die 7, the tubular member 9 is fixed inside the inner die 7, and the blade wire 5 is inserted so as to pass through the through-hole 14 of the tubular member 9. That is, the die housed inside the outer die 8 is formed to have a double tube structure including the inner die 7 and the tubular member 9. Since rotation of the tubular member 9 about the axis $AX_1$ is inhibited, the blade wire 5 is prevented from being damaged even when the inner die 7 is rotated.

In order to reliably prevent the blade wire 5 from coming into contact with the rotating inner die 7, the front end 13b of the tubular member 9 is preferably located frontward in the conveyance direction of the blade wire 5 relative to the front end 22 of the inner die 7 as shown in FIG. 2. Further, the outer face near the front end 13b of the tubular member 9 is preferably flush with the outer face near the front end 22 of the inner die 7. In this embodiment, the outer face near the front end 13b of the tubular member 9 and the outer face near the front end 22 of the inner die 7 form a curved surface (peripheral surface) of a forward-tapered truncated cone corresponding to the shape of the inner face of the outer die 8. Since the outer face near the front end 13b of the tubular member 9 is flush with the outer face near the front end 22 of the inner die 7, dimensional variation in the gap between the inner face of the outer die 8 and each of the outer face near the front end 13b of the tubular member 9 and the outer face near the front end 22 of the inner die 7 is inhibited, whereby variation in the extrusion pressure of the resin from the extrusion hole 15 can be inhibited. Thus, dimensional stability of the resin layer formed on the surface of the blade wire 5 can be improved.

The aforementioned die 1 is preferably used in combination with the mixing valve 3 according to the first embodiment or the second embodiment. Although details will be described later, each of the mixing valves according to the first embodiment and the second embodiment is characterized in that pressure variations in a first-resin flow path from the first extruder 2a to the die 1 and in a second-resin flow path from the second extruder 2b to the die 1 are inhibited, whereby accuracy of the rate of change in the mixing ratio of the two kinds of resins forming the resin layer (outer layer tube) and accuracy of the outer diameter of the resin layer are improved. When the aforementioned die 1 is combined with the mixing valve 3 according to the first embodiment or the second embodiment, the two kinds of resins supplied to the die 1 can be uniformly kneaded. Thus, accuracy of the rate of change in the mixing ratio of the resins forming the resin layer of the molded flexible tube and accuracy of the outer diameter dimension of the resin layer can be improved, and the mixing ratio of the resins in the resin layer can be continuously and smoothly changed along the longitudinal direction of the flexible tube 6.

Details of Mixing Valve According to the First Embodiment

Hereinafter, details of the mixing valve 3 according to the present embodiment will be described with reference to FIG. 3 to FIG. 10.

Figure 3:
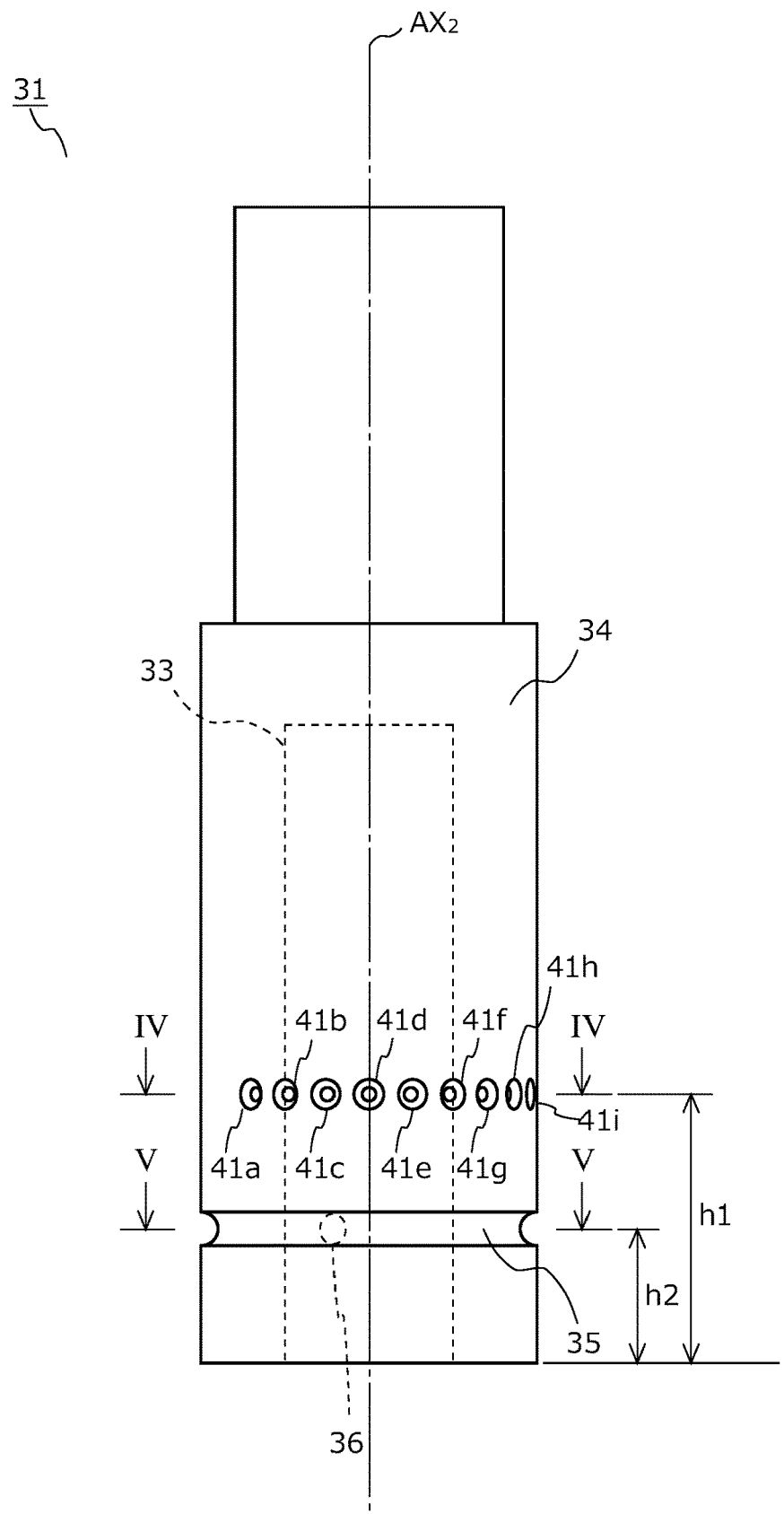
FIG. 3 is a front view of a first cylinder shown in FIG. 1.
Figure 4:
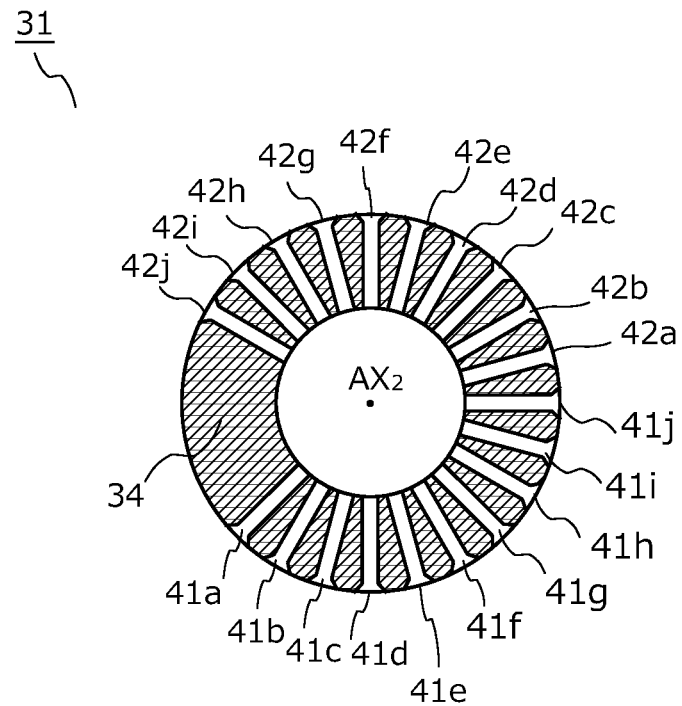
FIG. 4 is a cross-sectional view taken along a line IV-IV shown in FIG. 3.
Figure 5:
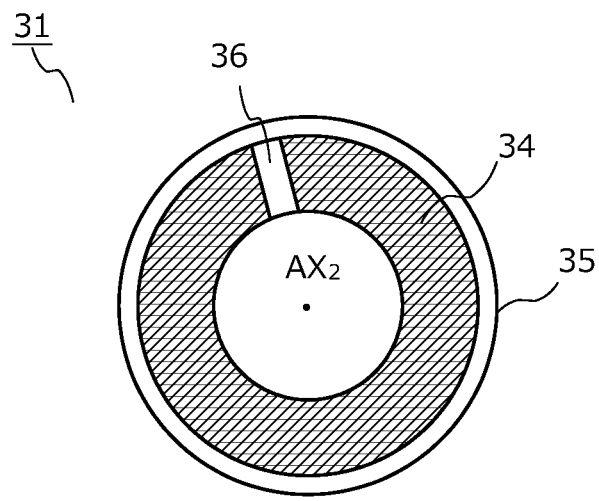
FIG. 5 is a cross-sectional view taken along a line V-V shown in FIG. 3.

FIG. 3 is a front view of the first cylinder shown in FIG. 1. FIG. 4 is a cross-sectional view taken along a line IV-IV shown in FIG. 3. FIG. 5 is a cross-sectional view taken along a line V-V shown in FIG. 3.

The first cylinder 31 is a cylindrical member having one end (lower end in FIG. 3) being open and the other end being closed. A space 33 having a columnar shape that is substantially the same as the outer shape of the second cylinder 32 is provided inside the first cylinder 31, whereby a peripheral wall portion 34 is formed. The first cylinder 31 is formed by cutting a metal, for example.

The first cylinder 31 is provided with a plurality of through-holes 41a to 41j and 42a to 42j which penetrate the peripheral wall portion 34 in radial directions. As shown in FIG. 3 and FIG. 4, the through-holes 41a to 41j and 42a to 42j have the same shape and the same inner diameter, and are provided at a constant pitch in the circumferential direction of the first cylinder 31 such that the center axes thereof are located at a height h1 from the lower end of the first cylinder 31, the center axes thereof extend in the radial directions of the first cylinder 31, and a center angle formed by adjacent center axes is constant. These through-holes 41a to 41j and 42a to 42j are supplied with the resin ejected from the first extruder 2a or the second extruder 2b. In the first valve 11, an opening formed in the outer peripheral surface of the peripheral wall portion 34 by providing each of the through-holes 41a to 41j and 42a to 42j corresponds to a "first opening". In the second valve 12, an opening formed in the outer peripheral surface of the peripheral wall portion 34 by providing each of the through-holes 41a to 41j and 42a to 42j corresponds to a "second opening".

As shown in FIG. 3 and FIG. 5, a discharge groove 35 having a width in the up-down direction relative to the position at a height h2 from the lower end of the first cylinder 31 is formed in the outer peripheral surface of the first cylinder 31. In addition, a through-hole 36 penetrating the peripheral wall portion 34 in the radial direction of the first cylinder 31 is formed in the discharge groove 35. The discharge groove 35 and the through-hole 36 are used for discharging (discarding), to the outside, unnecessary resins that are not supplied to the die 1.

Figure 6:
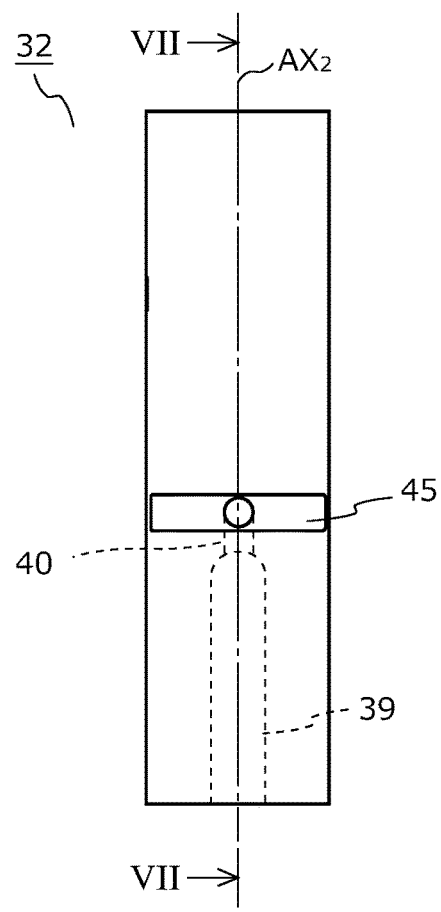
FIG. 6 is a front view of a second cylinder shown in FIG. 1.
Figure 7:
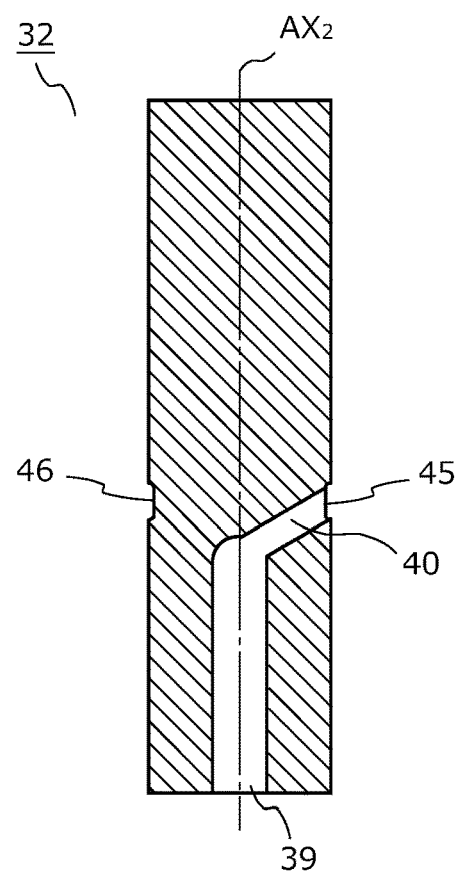
FIG. 7 is a cross-sectional view taken along a line VII-VII shown in FIG. 6.
Figure 8:
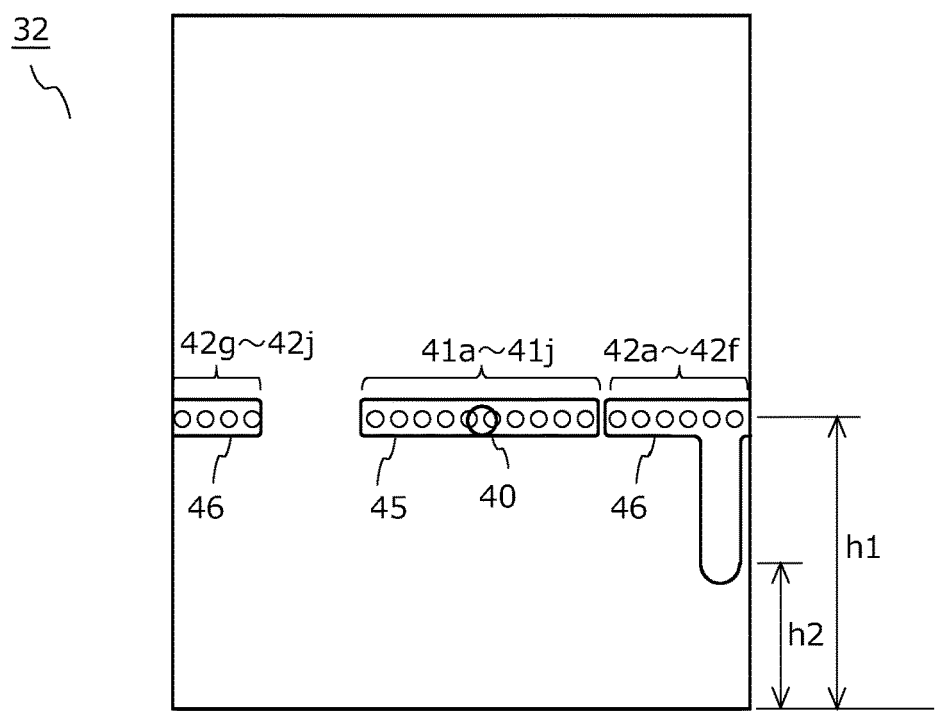
FIG. 8 is a development of the outer face of the second cylinder shown in FIG. 6.

FIG. 6 is a front view of the second cylinder shown in FIG. 1. FIG. 7 is a cross-sectional view taken along a line VII-VII shown in FIG. 6. FIG. 8 is a development of the outer face of the second cylinder shown in FIG. 6. In FIG. 8, small circles are drawn with thin lines in grooves 45 and 46. These circles do not denote structures provided in the second cylinder 32, but denote the positions to which inner-side openings of the through-holes 41a to 41j and 42a to 42j provided in the first cylinder 31 are opposed when the second cylinder 32 is inserted in the first cylinder 31 to be positioned.

The second cylinder 32 is a member having a substantially columnar shape. As shown in FIG. 6 and FIG. 7, inside the second cylinder 32, a long hole 39 is provided which extends from one end (lower end in FIG. 6 and FIG. 7) of the second cylinder 32 along the center axis to a predetermined height. The long hole 39 functions as a resin supply path for supplying the resin to the die 1. As shown in FIG. 6 and FIG. 8, grooves 45 and 46 are provided in the outer peripheral surface of the second cylinder 32. Further, as shown in FIGS. 6 to 8, the second cylinder 32 is provided with a flow-in path 40 that extends from the inside of the groove 45 to the long hole 39. The flow-in path 40 is a flow path for sending the resin supplied to the groove 45, into the long hole 39. The second cylinder 32 is also formed by cutting a metal, for example.

The groove 45 is composed of a portion that has a width in the up-down direction with respect to the level of the height h1 from the lower end of the second cylinder 32 and that extends in the circumferential direction of the second cylinder 32. In the state where the second cylinder 32 is inserted in the space 33 inside the first cylinder 31 to be positioned, as shown in FIG. 8, the inner-side openings of the through-holes 41a to 41j of the first cylinder 31 are opposed to the portion, of the groove 45, that extends in the circumferential direction.

The groove 46 is composed of: a portion that has a width in the up-down direction with respect to the level of the height h1 from the lower end of the second cylinder 32 and that extends in the circumferential direction of the second cylinder 32; and a portion that extends in the axial direction of the second cylinder 32 and that reaches the position at the height h2 from the lower end of the second cylinder 32. In the state where the second cylinder 32 is inserted in the space 33 inside the first cylinder 31 to be positioned, as shown in FIG. 8, the inner-side openings of the through-holes 42a to 42j of the first cylinder 31 are opposed to the portion, of the groove 46, that extends in the circumferential direction. The lower end of the portion, of the groove 46, that extends in the axial direction is opposed to the through-hole 36 of the first cylinder 31 shown in FIG. 3, in the state where the second cylinder 32 is inserted in the space 33 inside the first cylinder 31 to be positioned.

In the state where the valve body 16 is formed by combining the first cylinder 31 and the second cylinder 32, the grooves 45 and 46 formed in the second cylinder 32 are supplied with the resin through any of the through-holes 41a to 41j provided in the first cylinder 31. The groove 45, which is connected to the long hole 39 via the flow-in path 40, functions as a resin supply path, and the groove 46, which is connected to the through-hole 36 and to the discharge groove 35 of the first cylinder 31, functions as a resin discharge path. This point will be described later.

Figure 9:
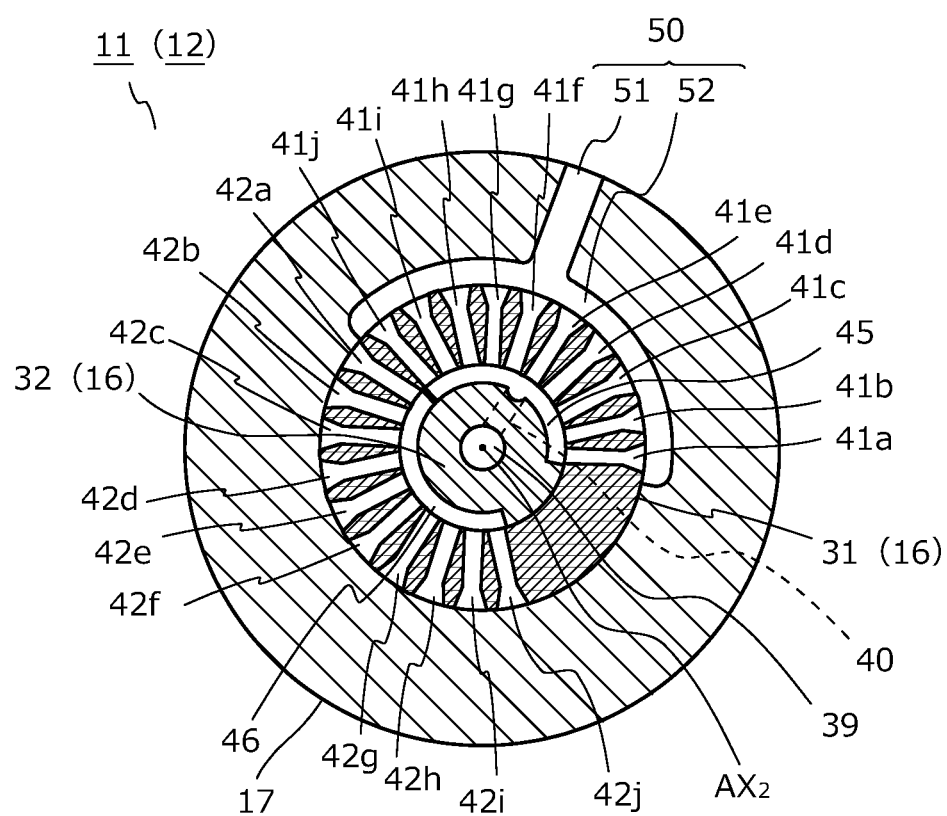
FIG. 9 is a cross-sectional view of a first valve shown in FIG. 1.

FIG. 9 is a cross-sectional view of the first valve shown in FIG. 1. FIG. 9 corresponds to a cross-sectional view taken along a line A-A' shown in FIG. 1.

The first valve 11 shown in FIG. 9 is formed by inserting, into the housing space inside the valve case 17, the valve body 16 in which the second cylinder 32 is inserted in the first cylinder 31 and these cylinders are fixed. As described above, the housing space inside the valve case 17 is formed in a columnar shape that is substantially the same as the shape of the outer peripheral surface of the valve body 16 (first cylinder 31). The valve body 16 is rotatable about the axis $AX_2$ with its outer peripheral surface sliding relative to the inner peripheral surface of the valve case 17.

In assembling the valve body 16, as described above, the rotational position of the second cylinder 32 with respect to the first cylinder 31 is determined such that the inner-side openings of the through-holes 41a to 41j of the first cylinder 31 are opposed to the groove 45 of the second cylinder 32 while the inner-side openings of the through-holes 42a to 42j of the first cylinder 31 are opposed to the groove 46 of the second cylinder 32 (see FIG. 3 to FIG. 8). When the first cylinder 31 and the second cylinder 32 are positioned as described above and fixed together, flow paths as follows are formed in the valve body 16.

(1) Resin Supply Path to the Die

A flow path extending from the through-holes 41a to 41j via the groove 45 and the flow-in path 40 to the long hole 39.

(2) Resin Discharge Path to the Outside

A flow path extending from the through-holes 42a to 42j via the groove 46 and the through-hole 36 to the discharge groove 35.

Meanwhile, as shown in FIG. 9, a supply path 50 is formed in the valve case 17. The supply path 50 is composed of: a flow path 51 to which the resin ejected from the extruder is supplied; and a groove-like flow path 52 which is connected to the flow path 51 and extends over a predetermined range in the circumferential direction of the inner peripheral surface of the valve case 17. The flow path 52 of the supply path 50 is formed at a position where the flow path 52 can be opposed to the through-holes 41a to 41j and 42a to 42j of the first cylinder 31.

The length in the circumferential direction of the flow path 52 provided in the inner peripheral surface of the valve case 17 is set such that the flow path 52 can communicate with a predetermined number of through-holes among the through-holes 41a to 41j and 42a to 42j. In the present embodiment, the length of the flow path 52 provided in the inner peripheral surface of the valve case 17 is set such that the flow path 52 can supply the resin to half (ten in the present embodiment) of the total number of the through-holes 41a to 41j and 42a to 42j.

Although details will be described later, when the valve body 16 is rotated about the axis $AX_2$, the positional relationship between the flow path 52 and the through-holes 41a to 41j and 42a to 42j changes. As described above, the through-holes 41a to 41j are connected to the resin discharge path, and the through-holes 42a to 42j are connected to the resin supply path to the die 1. Therefore, when the positional relationship between the flow path 52 and the through-holes 41a to 41j and 42a to 42j is changed by a rotation angle corresponding to one through-hole, the ratio of the number of the through-holes connected to the resin discharge path to the number of the through-holes connected to the resin supply path changes although the number of the through-holes communicating with the flow path 52 does not change. That is, by rotating the valve body 16, the distribution ratio of the resin to be supplied to the resin supply path to the die to the resin to be discharged to the outside can be changed. In the present embodiment, the number of the through-holes to which the flow path 52a can supply the resin at the same time, the number of the through-holes 41a to 41j connected to the resin supply path, and the number of the through-holes 42a to 42j connected to the resin discharge path are all 10. Therefore, the distribution ratio of the resin to be supplied to the resin supply path to the die to the resin to be discharged to the outside can be controlled in 11 levels within the range from 0:10 to 10:0.

The configuration of the second valve 12 shown in FIG. 1 is identical to that of the first valve 11, and a cross-sectional view thereof taken along a line B-B' shown in FIG. 1 is also identical to that shown in FIG. 9. Therefore, repeated description for the second valve 12 is not necessary.

Operation of Mixing Valve

Figure 10:
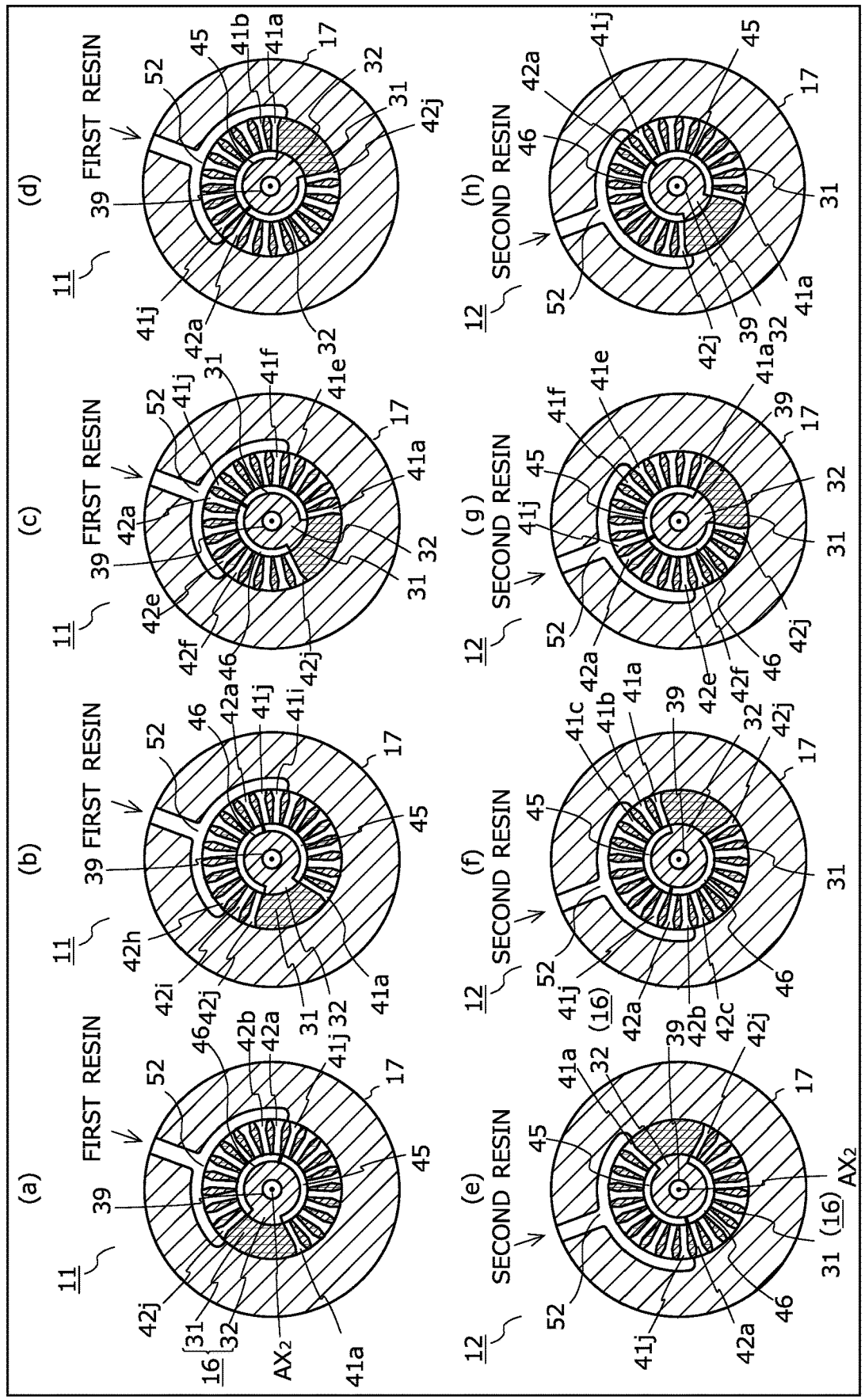
FIG. 10 shows diagrams for describing a method of adjusting a resin mixing ratio by using the mixing valve shown in FIG. 1.

FIG. 10 shows diagrams for describing a method of adjusting a resin mixing ratio by using the mixing valve shown in FIG. 1. In FIG. 10, (a) to (d) each show a cross section corresponding to a position along the line A-A' shown in FIG. 1, and (e) to (h) each show a cross section corresponding to a position along the line B-B' shown in FIG. 1. For convenience in drawing, reference characters of the through-holes are omitted as appropriate. However, in each of (a) to (h) of FIG. 10, the through-holes 41a to 41j and 42a to 42j are arranged in the counterclockwise direction about the axis $AX_2$. In FIG. 10, portions having the same hatching pattern represent the same members, and reference characters thereof are not indicated as appropriate.

State 1-1

First, (a) of FIG. 10 shows a state where the flow path 52 for the first resin communicates with all of the through-holes 42a to 42j of the first cylinder 31. In this state, all of the first resin supplied from the first extruder 2a through the flow path 52 flows from the through-holes 42a to 42j of the first cylinder 31 to the groove 46 of the second cylinder 32, and is discharged (discarded) to the outside through the through-hole 36 and the discharge groove 35 of the first cylinder 31 (see FIG. 3 to FIG. 8).

The rotational positions of the valve bodies 16 of the first valve 11 and the second valve 12 are synchronously controlled such that the number of the through-holes connected to the flow path 52 to which the first resin is supplied and the number of the through-holes connected to the flow path 52 to which the second resin is supplied, are the same fixed number (ten in the present embodiment). It is assumed that the number of the through-holes to which the flow path 52 can supply the resin at the same time is n (n: positive integer) and the number of the through-holes communicating with the flow path 52 in the first valve 11 is m (m: positive integer). The first valve 11 and the second valve 12 are controlled such that, when the distribution ratio of resins in the first valve 11 is m:(n-m), the distribution ratio of resins in the second valve 12 becomes (n-m):m. The distribution ratio of resins is the "ratio of the amount of the resin to be supplied to the die 1 to the amount of the resin to be discharged to the outside".

When the valve body 16 of the first valve 11 is at the rotational position shown in (a) of FIG. 10, the valve body 16 of the second valve 12 is disposed at the rotational position shown in (e) of FIG. 10. In this state, the flow path 52 to which the second resin is supplied communicates with all of the through-holes 41a to 41j of the first cylinder 31. Therefore, all of the second resin supplied from the second extruder 2b through the flow path 52 flows from the through-holes 41a to 41j of the first cylinder 31 to the groove 45 of the second cylinder 32, and is supplied to the die 1 through the flow-in path 40 and the long hole 39 of the second cylinder 32 (see FIG. 3 to FIG. 8).

That is, when the first valve 11 and the second valve 12 are controlled as shown in (a) and (e) of FIG. 10, all of the first resin is discharged to the outside while all of the second resin is supplied to the die 1, whereby the mixing ratio of the first resin to the second resin in the die 1 is 0:10.

State 1-2

Next, (b) of FIG. 10 shows a state where the valve body 16 of the first valve 11 is rotated, from the state shown in (a) of FIG. 10, in the counterclockwise direction about the axis $AX_2$ by an angle corresponding to two through-holes. As described above, the flow path 52 has a length that allows the flow path 52 to communicate with ten through-holes that are consecutive in the circumferential direction. Therefore, when the valve body 16 is rotated by an angle corresponding to two through-holes, communication of the flow path 52 with the two through-holes 42i and 42j at the most counterclockwise side is canceled, and the eight through-holes 42a to 42h of the first cylinder 31 and the two through-holes 41i and 41j consecutive thereto communicate with the flow path 52.

In this state, a portion, of the first resin supplied from the first extruder 2a through the flow path 52, that has been supplied to the through-holes 42a to 42h of the first cylinder 31 (8/10 of the supplied first resin) flows to the groove 46 of the second cylinder 32, and then is discharged to the outside. Meanwhile, the other portion of the first resin that has been supplied to the through-holes 41i and 41j (2/10 of the supplied first resin) flows to the groove 45 of the second cylinder 32, passes through the flow-in path 40, and flows into the long hole 39.

When the valve body 16 of the first valve 11 is at the rotational position shown in (b) of FIG. 10, the valve body 16 of the second valve 12 is disposed at the rotational position shown in (f) of FIG. 10. In this state, the flow path 52 to which the second resin is supplied communicates with the eight through-holes 41c to 41j of the first cylinder 31 and the two through-holes 42a and 42b consecutive thereto. A portion, of the second resin supplied from the second extruder 2b through the flow path 52, that has been supplied to the through-holes 41c to 41j of the first cylinder 31 (8/10 of the supplied second resin) flows from the through-holes 41c to 41j of the first cylinder 31 to the groove 45 of the second cylinder 32, and is supplied to the long hole 39 through the flow-in path 40 of the second cylinder. The other portion, of the second resin supplied from the flow path 52, that has been supplied to the through-holes 41a and 41b of the first cylinder 31 (2/10 of the supplied second resin) flows into the groove 46 of the second cylinder 32, and is discharged to the outside through the through-hole 36 and the discharge groove 35 of the first cylinder 31.

That is, when the first valve 11 and the second valve 12 are controlled as shown in (b) and (f) of FIG. 10, the first resin that has been supplied to two of the ten through-holes communicating with the flow path 52 of the first valve 11 and the second resin that has been supplied to eight of the ten through-holes communicating with the flow path 52 of the second valve 12, are supplied to the die 1. The other portions of the supplied resins are discharged to the outside. Therefore, when the respective valve bodies 16 are at the rotational positions shown in (b) and (f) of FIG. 10, the mixing ratio of the first resin to the second resin is 2:8.

State 1-3

Next, (c) of FIG. 10 shows a state where the valve body 16 of the first valve 11 is rotated, from the state shown in (b) of FIG. 10, in the counterclockwise direction about the axis $AX_2$ by an angle corresponding to three through-holes. As described above, the flow path 52 has a length that allows the flow path 52 to communicate with ten through-holes that are consecutive in the circumferential direction. Therefore, when the valve body 16 is rotated by the angle corresponding to three through-holes, communication of the three through-holes 42f to 42h with the flow path 52 is canceled, and the five through-holes 42a to 42e of the first cylinder 31 and the five through-holes 41f to 41j consecutive thereto communicate with the flow path 52.

In this state, a portion, of the first resin supplied from the first extruder 2a through the flow path 52, that has been supplied to the through-holes 42a to 42e of the first cylinder 31 (5/10 of the supplied first resin) flows to the groove 46 of the second cylinder 32, and then is discharged to the outside. Meanwhile, the other portion of the first resin that has been supplied to the through-holes 41f to 41j (5/10 of the supplied first resin) flows to the groove 45 of the second cylinder 32, passes through the flow-in path 40, and flows into the long hole 39.

When the valve body 16 of the first valve 11 is at the rotational position shown in (c) of FIG. 10, the valve body 16 of the second valve 12 is disposed at the rotational position shown in (g) of FIG. 10. In this state, the flow path 52 to which the second resin is supplied communicates with the five through-holes 41f to 41j of the first cylinder 31 and the five through-holes 42a to 42e consecutive thereto. A portion, of the second resin supplied from the second extruder 2b through the flow path 52, that has been supplied to the through-holes 41f to 41j of the first cylinder 31 (5/10 of the supplied second resin) flows from the through-holes 41f to 41j of the first cylinder 31 to the groove 45 of the second cylinder 32, and is supplied to the long hole 39 through the flow-in path 40 of the second cylinder. The other portion, of the second resin supplied from the flow path 52, that has been supplied to the through-holes 42a to 42e of the first cylinder 31 (5/10 of the supplied second resin) flows to the groove 46 of the second cylinder 32, and is discharged to the outside through the through-hole 36 and the discharge groove 35 of the first cylinder 31.

That is, when the first valve 11 and the second valve 12 are controlled as shown in (c) and (g) of FIG. 10, the first resin that has been supplied to five of the ten through-holes communicating with the flow path 52 of the first valve 11 and the second resin that has been supplied to five of the ten through-holes communicating with the flow path 52 of the second valve 12, are supplied to the die 1. The other portions of the supplied resins are discharged to the outside. Therefore, when the respective valve bodies 16 are at the rotational positions shown in (c) and (g) of FIG. 10, the mixing ratio of the first resin to the second resin is 5:5.

State 1-4

Next, (d) of FIG. 10 shows a state where the valve body 16 of the first valve 11 is rotated, from the state shown in (c) of FIG. 10, in the counterclockwise direction about the axis $AX_2$ by an angle corresponding to five through-holes. As described above, the flow path 52 has a length that allows the flow path 52 to communicate with ten through-holes that are consecutive in the circumferential direction. Therefore, when the valve body 16 is rotated by an angle corresponding to five through-holes, communication of the through-holes 42a to 42e with the flow path 52 is canceled, and the ten through-holes 41a to 41j of the first cylinder 31 communicate with the flow path 52.

In this state, all of the first resin supplied from the first extruder 2a through the flow path 52 flows to the groove 45 of the second cylinder 32, passes through the flow-in path 40, and flows into the long hole 39.

When the valve body 16 of the first valve 11 is at the rotational position shown in (d) of FIG. 10, the valve body 16 of the second valve 12 is disposed at the rotational position shown in (h) of FIG. 10. In this state, the flow path 52 to which the second resin is supplied communicates with the through-holes 42a to 42j of the first cylinder 31. Therefore, all of the second resin supplied from the second extruder 2b through the flow path 52 flows into the groove 46 of the second cylinder 32, and is discharged to the outside through the through-hole 36 and the discharge groove 35 of the first cylinder 31.

That is, when the first valve 11 and the second valve 12 are controlled as shown in (d) and (h) of FIG. 10, all of the first resin is supplied to the die 1 and all of the second resin is discharged to the outside, and therefore, the mixing ratio of the first resin to the second resin in the die 1 is 10:0.

In FIG. 10, the examples in which the mixing ratio of the first resin to the second resin is varied to be 0:10, 2:8, 5:5, and 10:0 have been representatively described. However, the first resin and the second resin can also be mixed at any mixing ratio ranging from 0:10 to 10:0, depending on the rotational position of the valve body 16. In addition, the mixing ratio can be adjusted within a desired range by increasing/decreasing the number of through-holes as appropriate.

As described above, in the flexible tube production apparatus 100 according to the present embodiment, the supply amount of the resins to the die 1 and the discharge amount of the resins to the outside are changed in the mixing valve 3, whereby the mixing ratio of the first resin to the second resin in the die 1 can be changed while keeping constant the total of the amount of the first resin to be supplied from the first valve 11 to the die 1 and the amount of the second resin to be supplied from the second valve 12 to the die 1. When the resin layer (outer layer tube) of the flexible tube is extrusion-molded with the valve bodies 16 of the first valve 11 and the second valve 12 being rotated, the mixing ratio of the first resin to the second resin, which form the resin layer, can be continuously changed. For example, if resins having different hardnesses are used as the first resin and the second resin, the hardness of the resin layer can be gradually increased or decreased from one end to the other end of the catheter shaft. Therefore, with the flexible tube production apparatus 100 according to the present embodiment, it is possible to produce a catheter shaft in which the property of the resin layer, such as the hardness, is naturally changed along the length direction thereof, in contrast to the conventional production method.

As a method of changing the resin mixing ratio, a method is conceivable in which the rotation speeds of the screws or gear pumps of the first extruder and the second extruder are changed to adjust the ejection amount (volume) per unit time. However, if the rotation speeds of the screws or the gear pumps are changed, pressure variation may occur in the resins that remain in the resin flow paths and the die. The pressure variation may cause variation in the amount of the resin extruded from the die, or may interfere with the accuracy when changing the mixing ratio of the resins to be supplied to the die. Therefore, in the case where the mixing ratio of the resins is controlled by adjusting the extrusion speeds of the first extruder and the second extruder, accuracy of the rate of change in the mixing ratio of the two kinds of resins forming the resin layer and/or accuracy of the outer-diameter dimension of the resin layer are degraded. In particular, in a catheter, such as a blood vessel catheter, whose outer diameter is about 0.5 to 1.8 mm, if the hardness and/or the outer diameter thereof deviate from design values, ability of the catheter to follow a bending portion of a blood vessel when the catheter is inserted into the blood vessel and/or operability of the catheter may be degraded. Meanwhile, in the flexible tube production apparatus 100 according to the present embodiment, since the mixing ratio of the first resin to the second resin is changed by changing the distribution ratio (ratio of the supply amount to the discharge amount) of each of the first resin and the second resin, the extrusion speeds of the first extruder and the second extruder need not be changed. Therefore, it is possible to inhibit pressure variations in the first-resin flow path extending from the first extruder 2a to the die 1 and in the second-resin flow path extending from the second extruder 2b to the die 1. Thus, volume variation in the resin extruded from the extrusion hole of the die 1 is inhibited, and the mixing ratio of the first resin to the second resin is controlled with good response, whereby accuracy of the rate of change in the mixing ratio of the two kinds of resins forming the resin layer and accuracy of the outer-diameter dimension of the resin layer can be improved.

Second Embodiment

Configuration of Flexible Tube Production Apparatus

Figure 11:
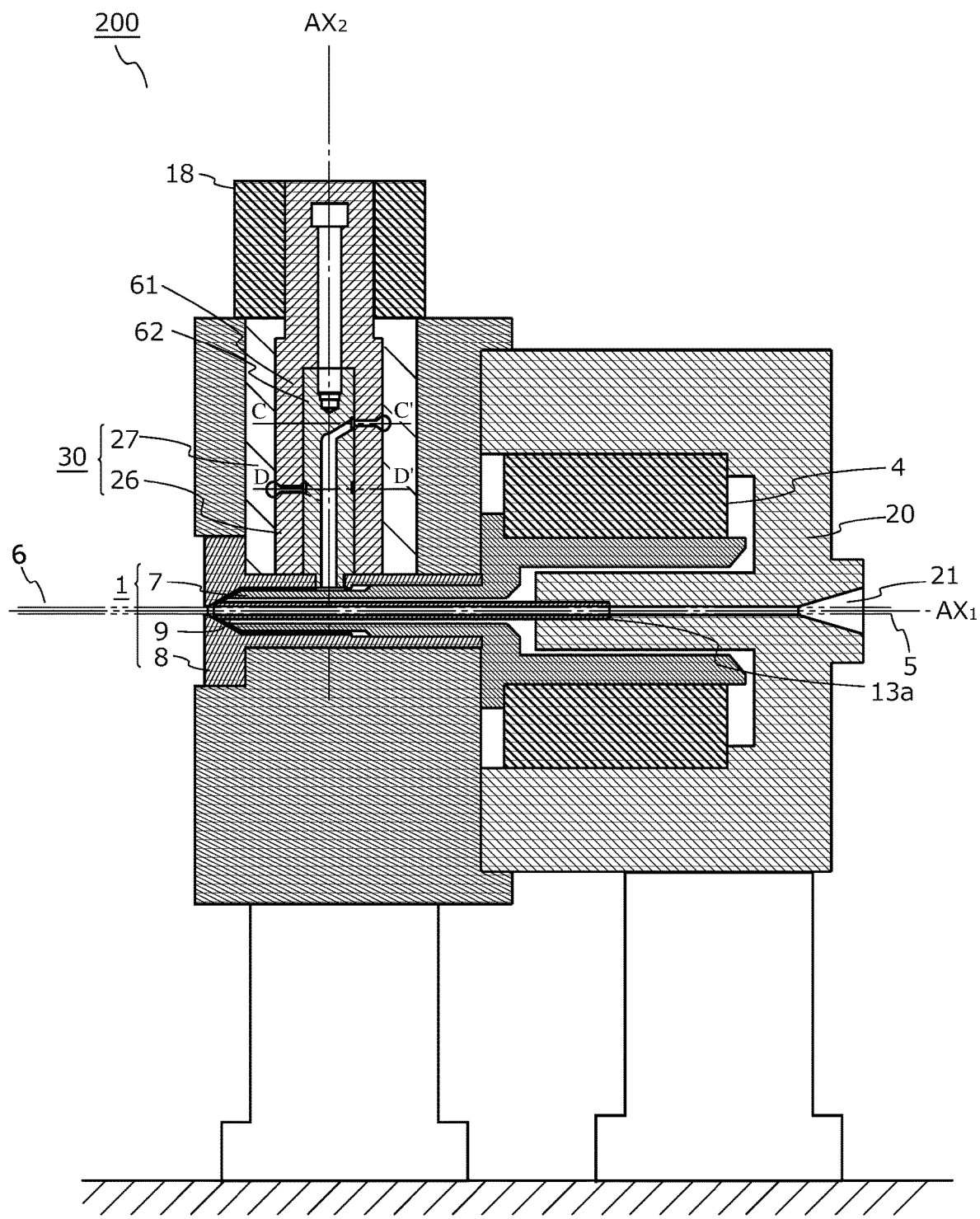
FIG. 11 is a vertical cross-sectional view showing the schematic configuration of a flexible tube production apparatus according to a second embodiment.

FIG. 11 is a vertical cross-sectional view showing a schematic configuration of a flexible tube production apparatus according to a second embodiment.

The flexible tube production apparatus 200 according to the present embodiment includes a die 1, a first extruder (not shown), a second extruder (not shown), a mixing valve 30, and a motor 4. The mixing valve 30 is supplied with a first resin and a second resin, which are different from each other, from the first extruder and the second extruder, respectively. The flexible tube production apparatus 200 is fixed to a predetermined mounting base or the like with a pedestal interposed therebetween. Although not shown, in the present embodiment, a supply device for supplying a blade wire 5 to the flexible tube production apparatus 200, a haul-off device for hauling off a flexible tube 6 that has been extrusion-molded, and the like are provided as appropriate at the upstream side and the downstream side of the flexible tube production apparatus 200.

The die 1 of the flexible tube production apparatus 200 includes an inner die 7, an outer die 8, and a tubular member 9 which are identical to those described in the first embodiment. The inner die 7 is connected to the motor 4 and is rotatable about the axis $AX_1$ as in the first embodiment. Although not shown, as in the first embodiment, a helical groove (not shown) for kneading melted resins is formed at the outer face of the inner die 7 (see FIG. 2). The outer die 8 surrounds the inner die 7 such that a predetermined gap is formed between the outer die 8 and the outer face of the inner die 7. The outer die 8 has, at a front end thereof, an extrusion hole for extruding the resins. The tubular member 9 has a through-hole through which the blade wire 5 is inserted. The tubular member 9 is housed inside the inner die 7.

In the present embodiment, during extrusion molding of a flexible tube, supply of the resins to the die 1 is performed while the inner die 7 is being rotated about the axis $AX_1$ by the motor 4. Since the helical groove (not shown) is formed at the outer face of the inner die 7, the resins supplied to the resin flow path between the outer face of the inner die 7 and the inner face of the outer die 8 are extruded from the extrusion hole 15 while being kneaded in accordance with the rotation of the inner die 7 about the axis $AX_1$. Therefore, with the flexible tube production apparatus 200 according to the present embodiment, when two kinds of resins are mixed and molded into a resin layer of a mixed-resin flexible tube, uniformization of the two kinds of resins can be achieved.

Details of Mixing Valve According to the Second Embodiment

The flexible tube production apparatus 200 according to the present embodiment is different from the flexible tube production apparatus 100 according to the first embodiment in the configuration of the mixing valve 30. More specifically, in the first embodiment, the mixing valve 3 is composed of two sets of the valve body 16 and the valve case 17 (i.e., the first valve 11 and the second valve 12). However, in the present embodiment, the mixing valve 30 is composed of one valve body 26 and one valve case 27. Hereinafter, the mixing valve 30 according to the present embodiment will be described in detail with reference to FIG. 11 to FIG. 20.

Figure 12:
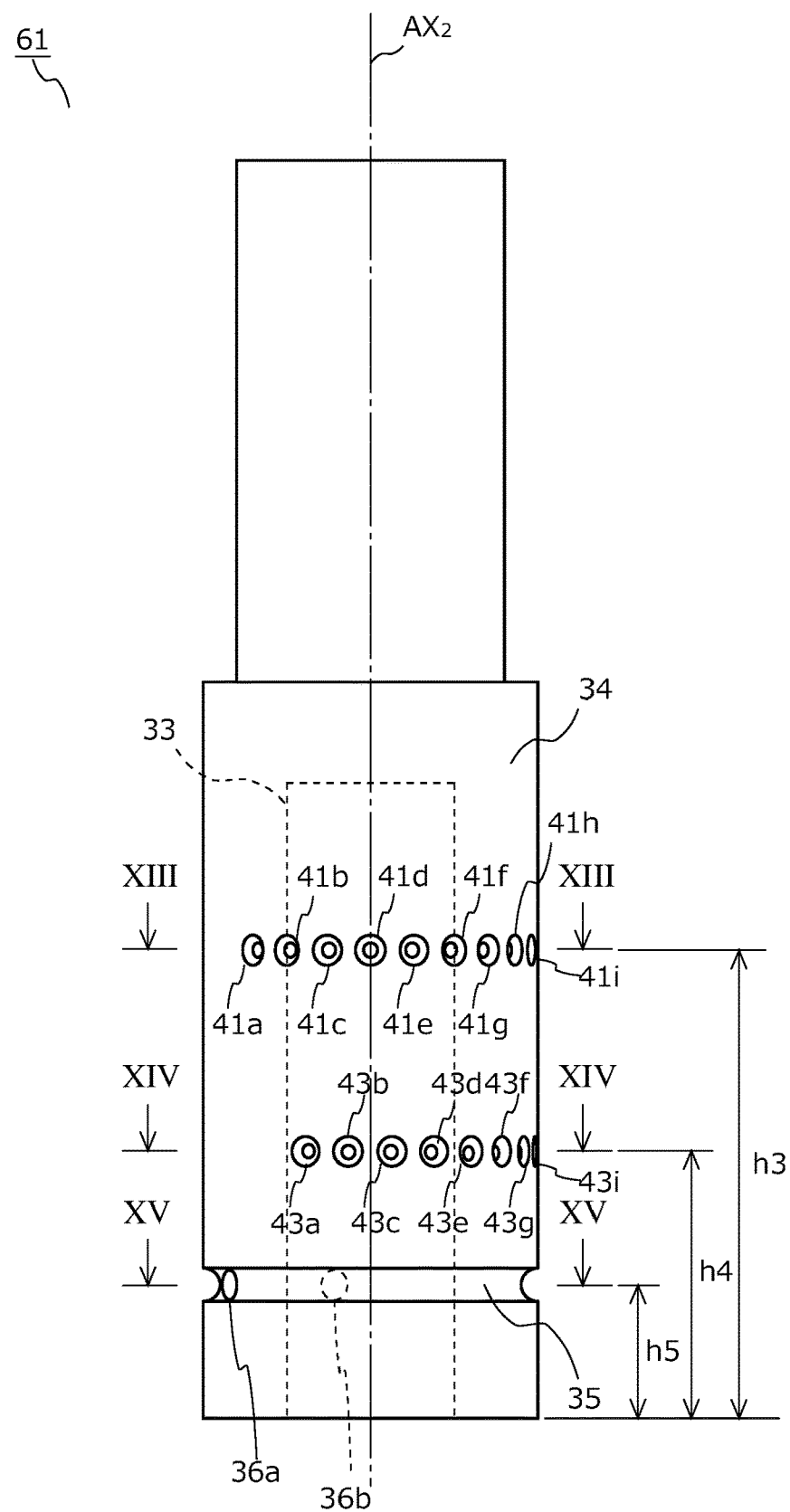
FIG. 12 is a front view of a first cylinder shown in FIG. 11.
Figure 13:
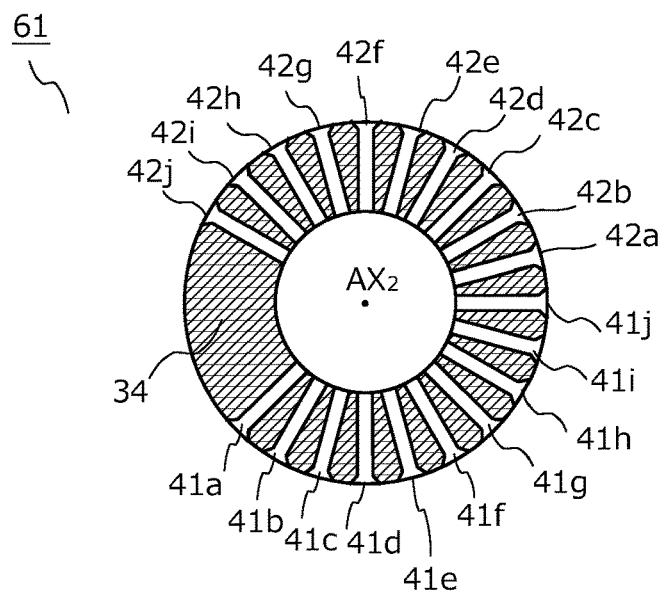
FIG. 13 is a cross-sectional view taken along a line XIII-XIII shown in FIG. 12.
Figure 14:
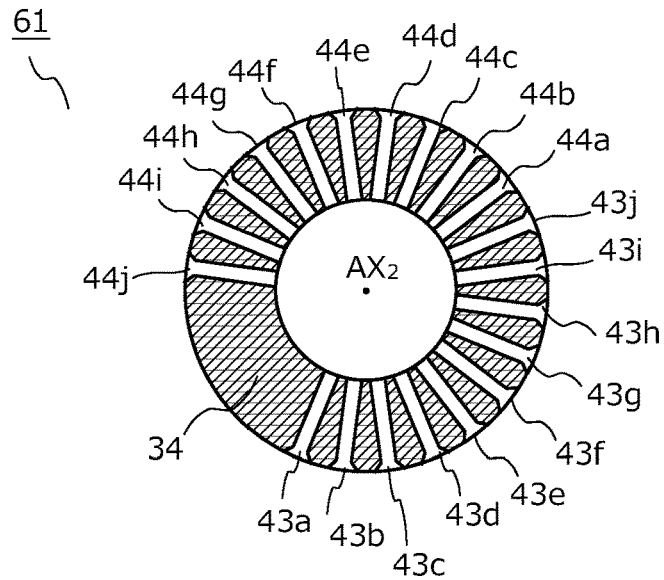
FIG. 14 is a cross-sectional view taken along a line XIV-XIV shown in FIG. 12.
Figure 15:
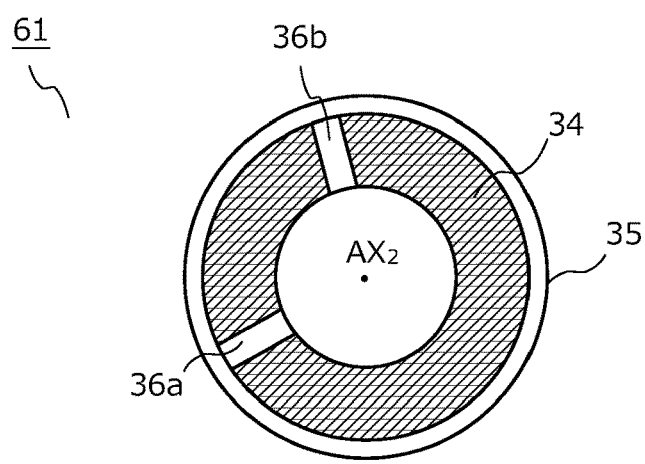
FIG. 15 is a cross-sectional view taken along a line XV-XV shown in FIG. 12.

FIG. 12 is a front view of the first cylinder shown in FIG. 11. FIG. 13 is a cross-sectional view taken along a line XIII-XIII shown in FIG. 12. FIG. 14 is a cross-sectional view taken along a line XIV-XIV shown in FIG. 12. FIG. 15 is a cross-sectional view taken along a line XV-XV shown in FIG. 12.

The mixing valve 30 includes a valve body 26, and a valve case 27 in which the valve body 26 is rotatably housed. The valve body 26 is composed of a hollow first cylinder 61, and a second cylinder 62 that is housed in the first cylinder 61 and is fixed to the first cylinder 61. Details of the first cylinder 61 and the second cylinder 62 will be described later. A space having a columnar shape that is substantially the same as the outer shape of the valve body 26 is provided in the valve case 27, and the valve body 26 is housed in this space. While being housed in the valve case 27, the valve body 26 is rotatably supported about the axis $AX_2$, with the outer peripheral surface of the valve body 26 sliding relative to the inner peripheral surface of the valve case 27. The valve body 26 is connected to a drive mechanism 18 such as a motor (see FIG. 11). The drive mechanism 18 rotates the valve body 26 about the axis $AX_2$ in accordance with control of a control device (not shown). The mixing valve 30 can change the mixing ratio of the first resin to the second resin to be supplied to the die 1, depending on the rotational position of the valve body 26.

The first cylinder 61 is a cylindrical member having one end (lower end in FIG. 12) being open and the other end being closed. A space 33 having a columnar shape that is substantially the same as the outer shape of the second cylinder 62 is provided inside the first cylinder 61, whereby a peripheral wall portion 34 is formed. The first cylinder 61 is formed by cutting a metal, for example.

The first cylinder 61 is provided with a plurality of through-holes 41a to 41j, 42a to 42j, 43a to 43j, and 44a to 44j which penetrate the peripheral wall portion 34 in radial directions.

As shown in FIG. 12 and FIG. 13, the through-holes 41a to 41j and 42a to 42j have the same shape and the same inner diameter, and are intermittently provided at a constant pitch in the circumferential direction of the first cylinder 61 such that the center axes thereof are located at a height h3 from the lower end of the first cylinder 61, the center axes extend in the radial directions of the first cylinder 61, and the respective center axes form a constant angle. These through-holes 41a to 41j and 42a to 42j are supplied with the first resin ejected from the first extruder. An opening formed in the outer peripheral surface of the peripheral wall portion 34 by providing each of the through-holes 41a to 41j and 42a to 42j corresponds to a "first opening".

As shown in FIG. 12 and FIG. 14, the through-holes 43a to 43j and 44a to 44j have the same shape and the same inner diameter as the through-holes 41a to 41j and 42a to 42j, and are provided at a constant pitch in the circumferential direction of the first cylinder 61 such that the center axes thereof are located at a height h4 from the lower end of the first cylinder 61, the center axes extend in the radial directions of the first cylinder 61, and the respective center axes form a constant angle. These through-holes 43a to 43j and 44a to 44j are supplied with the second resin ejected from the second extruder. An opening formed in the outer peripheral surface of the peripheral wall portion 34 by providing each of the through-holes 43a to 43j and 44a to 44j corresponds to a "second opening".

As shown in FIG. 12 and FIG. 15, a discharge groove 35 having a width in the up-down direction with respect to the position at a height h5 from the lower end of the first cylinder 61 is formed in the outer peripheral surface of the first cylinder 61. In addition, through-holes 36a and 36b penetrating the peripheral wall portion 34 in the radial directions of the first cylinder 61 are formed in the discharge groove 35. The discharge groove 35 and the through-holes 36a and 36b are used for discharging (discarding), to the outside, unnecessary resins that are not supplied to the die.

Figure 16:
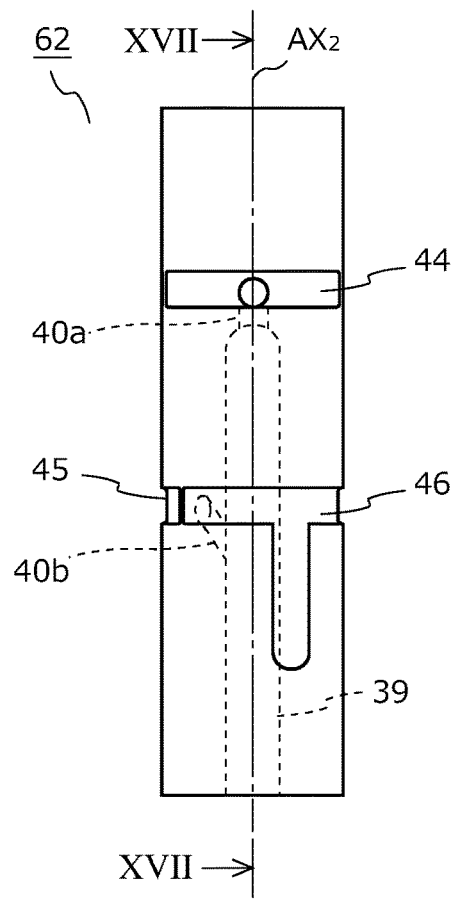
FIG. 16 is a front view of a second cylinder shown in FIG. 11.
Figure 17:
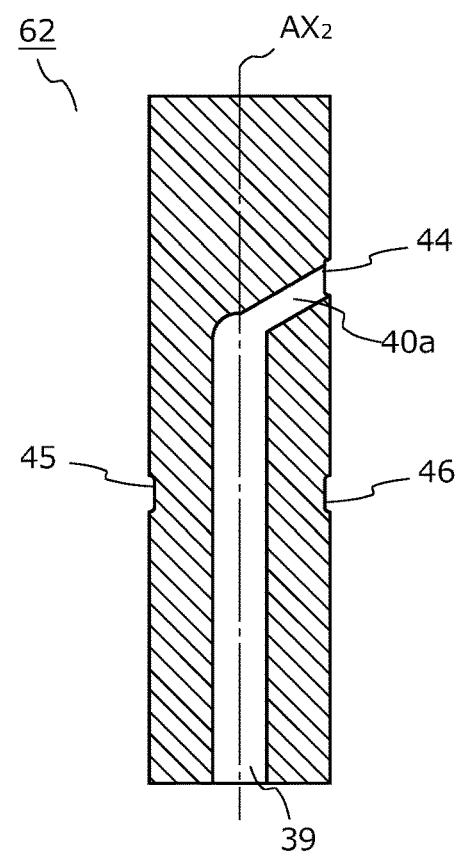
FIG. 17 is a cross-sectional view taken along a line XVII-XVII shown in FIG. 16.
Figure 18:
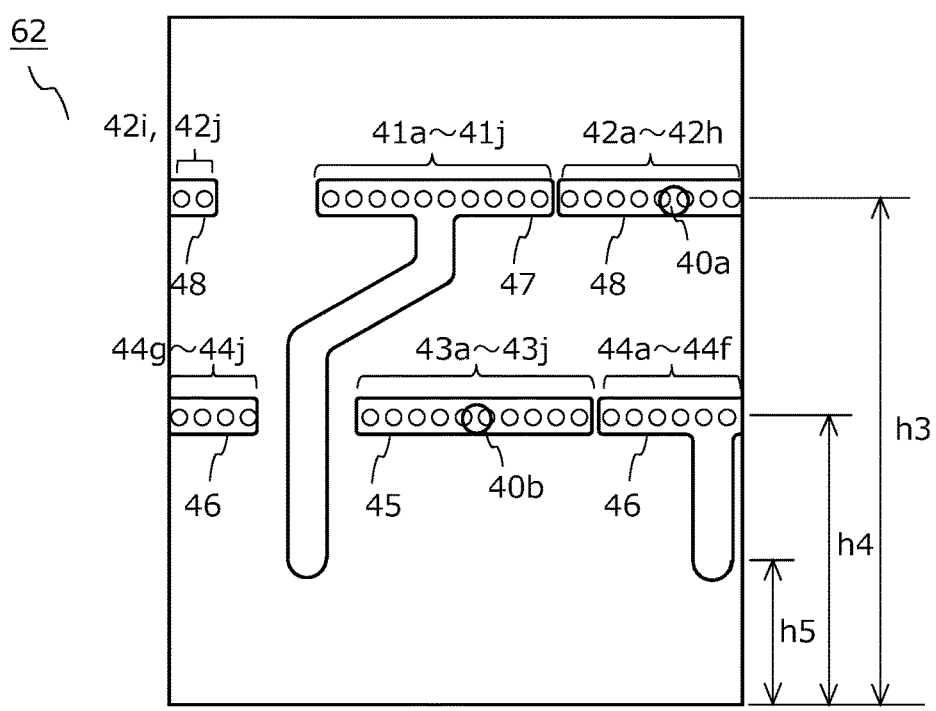
FIG. 18 is a development of the outer face of a second cylinder shown in FIG. 16.

FIG. 16 is a front view of the second cylinder shown in FIG. 11. FIG. 17 is a cross-sectional view taken along a line XVII-XVII shown in FIG. 16. FIG. 18 is a development of the outer face of the second cylinder shown in FIG. 16. In FIG. 18, small circles are drawn with thin lines in the grooves 45 to 48. These circles do not denote structures provided in the second cylinder 62, but denote the positions to which inner-side openings of the through-holes 41a to 41j, 42a to 42j, 43a to 43j, and 44a to 44j provided in the first cylinder 61 are opposed when the second cylinder 62 is inserted in the first cylinder 61 to be positioned.

The second cylinder 62 is a member having a substantially columnar shape. As shown in FIG. 16 and FIG. 17, inside the second cylinder 62, a long hole 39 is provided which extends from one end (lower end in FIG. 16 and FIG. 17) of the second cylinder 62 along the center axis to a predetermined height. The long hole 39 functions as a resin supply path for supplying the resin to the die 1. As shown in FIG. 16 and FIG. 18, a plurality of grooves 45 to 48 are provided in the outer peripheral surface of the second cylinder 62. Further, as shown in FIG. 16 to FIG. 18, the second cylinder 62 is provided with a flow-in path 40a that extends from the inside of the groove 48 to the long hole 39, and a flow-in path 40b that extends from the inside of the groove 45 to the long hole 39. The flow-in path 40a is a flow path for sending the first resin supplied to the groove 48, into the long hole 39. The flow-in path 40b is a flow path for sending the second resin supplied to the groove 45, into the long hole 39. The second cylinder 62 is also formed by cutting a metal, for example.

The groove 47 is composed of: a portion that has a width in the up-down direction with respect to the level of the height h3 from the lower end of the second cylinder 62 and that extends in the circumferential direction of the second cylinder 62; and a portion that extends in the axial direction of the second cylinder 62 and that reaches the position at the height h5 from the lower end of the second cylinder 62. In the state where the second cylinder 62 is inserted in the space 33 inside the first cylinder 61 to be positioned, as shown in FIG. 18, the inner-side openings of the through-holes 41a to 41j of the first cylinder 61 are opposed to the portion, of the groove 47, that extends in the circumferential direction. The lower end of the portion, of the groove 47, that extends in the axial direction is opposed to the through-hole 36a of the first cylinder 61 shown in FIG. 12, in the state where the second cylinder 62 is inserted in the space 33 inside the first cylinder 61 to be positioned.

The groove 48 is composed of a portion that has a width in the up-down direction with respect to the level of the height h3 from the lower end of the second cylinder 62 and that extends in the circumferential direction of the second cylinder 62. In the state where the second cylinder 62 is inserted in the space 33 inside the first cylinder 61 to be positioned, as shown in FIG. 18, the inner-side openings of the through-holes 42a to 42j of the first cylinder 61 are opposed to the portion, of the groove 48, that extends in the circumferential direction.

In the state where the valve body 26 is formed by combining the first cylinder 61 and the second cylinder 62, the grooves 47 and 48 formed in the second cylinder 62 are supplied with the first resin through any of the through-holes 41a to 41j and 42a to 42j provided in the first cylinder 61. Specifically, the groove 47 functions as a first-resin discharge path, and the groove 48 functions as a first-resin supply path. This point will be described later.

The groove 45 is composed of a portion that has a width in the up-down direction with respect to the level of the height h4 from the lower end of the second cylinder 62 and that extends in the circumferential direction of the second cylinder 62. In the state where the second cylinder 62 is inserted in the space 33 inside the first cylinder 61 to be positioned, as shown in FIG. 18, inner-side openings of the through-holes 43a to 43j of the first cylinder 61 are opposed to the portion, of the groove 45, that extends in the circumferential direction.

The groove 46 is composed of: a portion that has a width in the up-down direction with respect to the level of the height h4 from the lower end of the second cylinder 62 and that extends in the circumferential direction of the second cylinder 62; and a portion that extends in the axial direction of the second cylinder 62 and that reaches the position at the height h5 from the lower end of the second cylinder 62. In the state where the second cylinder 62 is inserted in the space 33 inside the first cylinder 61 to be positioned, as shown in FIG. 18, inner-side openings of the through-holes 44a to 44j of the first cylinder 61 are opposed to the position, of the groove 46, that extends in the circumferential direction. In the state where the second cylinder 62 is inserted in the space 33 inside the first cylinder 61 to be positioned, the lower end of the portion, of the groove 46, that extends in the axial direction is opposed to the through-hole 36b of the first cylinder 61 shown in FIG. 12.

In the state where the valve body 26 is formed by combining the first cylinder 61 and the second cylinder 62, the second resin is supplied to the grooves 45 and 46 formed in the second cylinder 62 through any of the through-holes 43a to 43j and 44a to 44j provided in the first cylinder 61. Specifically, the groove 45 functions as a second-resin supply path, and the groove 46 functions as a second-resin discharge path. This point will be described later.

Figure 19:
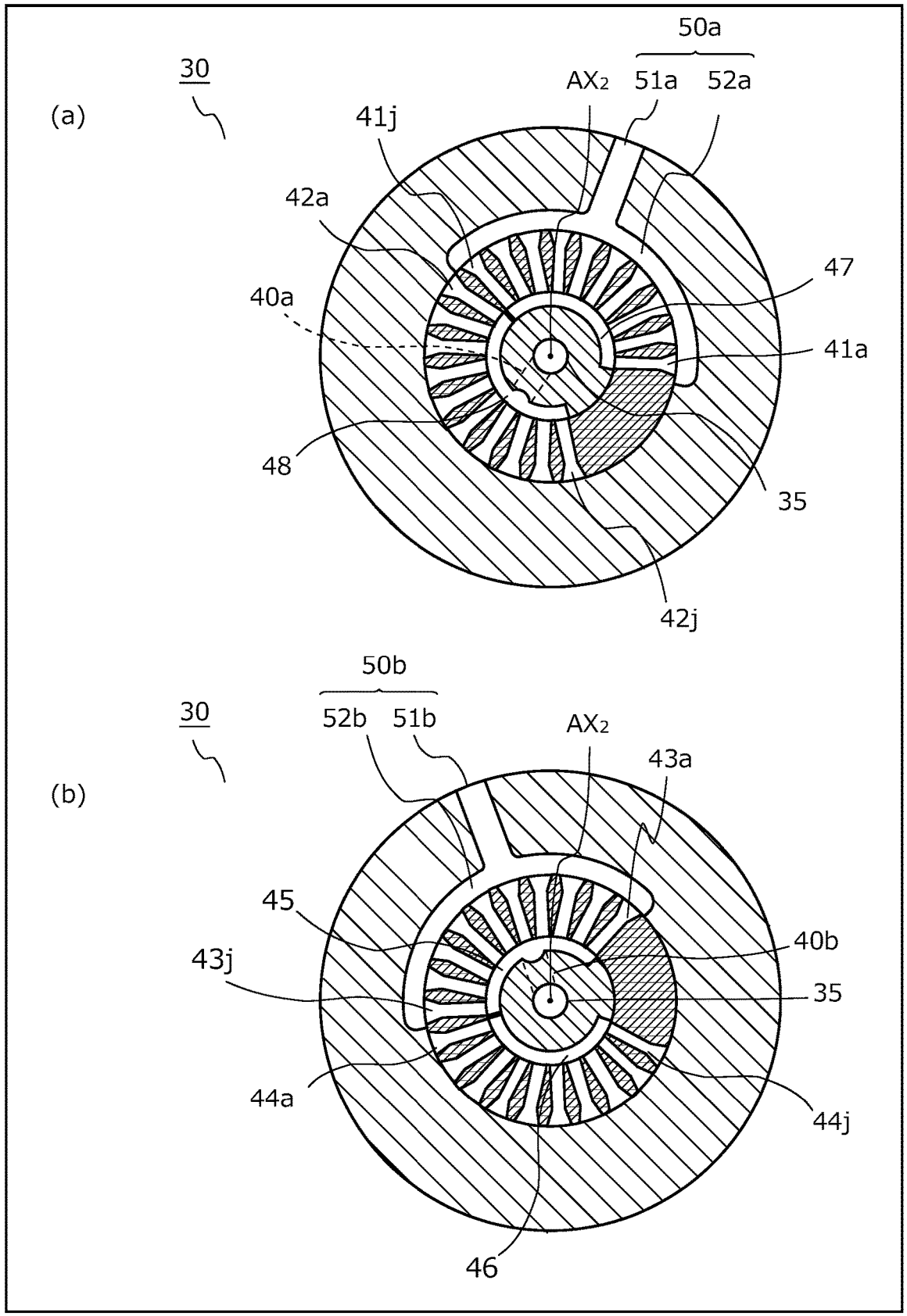
FIG. 19 shows cross-sectional views of a mixing valve according to the second embodiment.

FIG. 19 shows cross-sectional views of the mixing valve according to the second embodiment. More specifically, (a) of FIG. 19 corresponds to a cross-sectional view taken along a line C-C' in FIG. 11, and (b) of FIG. 19 corresponds to a cross-sectional view taken along a line D-D' in FIG. 11. For convenience in drawing, reference characters of the through-holes are omitted as appropriate. However, in (a) of FIG. 19, the through-holes 41a to 41j and 42a to 42j are arranged in the counterclockwise direction about the axis $AX_2$, as in FIG. 13. In (b) of FIG. 19, the through-holes 43a to 43j and 44a to 44j are arranged in the counterclockwise direction about the axis $AX_2$, as in FIG. 14.

The mixing valve 30 shown in FIG. 11 is obtained by inserting, into an accommodating space inside the valve case 27, the valve body 26 in which the second cylinder 62 is inserted inside the first cylinder 61 so as to fix the relative rotation therebetween. As described above, the accommodating space inside the valve case 27 is formed in a columnar shape that is substantially the same as the shape of the outer peripheral surface of the valve body 26 (first cylinder 61). The valve body 26 is rotatable about the axis $AX_2$ with its outer peripheral surface sliding relative to the inner peripheral surface of the valve case 27.

In assembling the valve body 26, as described with reference to FIG. 18, the rotational position of the second cylinder 62 relative to the first cylinder 61 is determined such that the inner-side openings of the through-holes 41a to 41j of the first cylinder 61 are opposed to the groove 47 of the second cylinder 62, the inner-side openings of the through-holes 42a to 42j of the first cylinder 61 are opposed to the groove 48 of the second cylinder 62, the inner-side openings of the through-holes 43a to 43j of the first cylinder 61 are opposed to the groove 45 of the second cylinder 62, and the inner-side openings of the through-holes 44a to 44j of the first cylinder 61 are opposed to the groove 46 of the second cylinder 62 (see FIG. 12 to FIG. 18). When the first cylinder 61 and the second cylinder 62 are fixed through the aforementioned positioning, flow paths as follows are formed in the valve body 26.

(1) Resin Supply Path for the First Resin to the Die

A flow path extending from the through-holes 42a to 42j to the long hole 39 through the groove 48 and the flow-in path 40a.

(2) Resin Discharge Path for the First Resin to the Outside

A flow path extending from the through-holes 41a to 41j to the discharge groove 35 through the groove 47 and the through-hole 36a.

(3) Resin Supply Path for the Second Resin to the Die

A flow path extending from the through-holes 43a to 43j to the long hole 39 through the groove 45 and the flow-in path 40b.

(4) Resin Discharge Path for the Second Resin to the Outside

A flow path extending from the through-holes 44a to 44j to the discharge groove 35 through the groove 46 and the through-hole 36b.

Meanwhile, as shown in FIG. 19, supply paths 50a and 50b are formed in the valve case 27. The supply path 50a is composed of: a flow path 51a to which the resin ejected from the first extruder is supplied; and a groove-like flow path 52a which is connected to the flow path 51a and extends over a predetermined range in the circumferential direction of the inner peripheral surface of the valve case 17. The flow path 52a of the supply path 50a is formed at a position where the flow path 52a can be opposed to the through-holes 41a to 41j and 42a to 42j of the first cylinder 61. In addition, the supply path 50b is composed of: a flow path 51b to which the resin ejected from the first extruder is supplied; and a groove-like flow path 52b which is connected to the flow path 51b and extends over a predetermined range in the circumferential direction of the inner peripheral surface of the valve case 17. The flow path 52b of the supply path 50b is formed at a position where the flow path 52b can be opposed to the through-holes 43a to 43j and 44a to 44j of the first cylinder 61.

The lengths of the flow paths 52a and 52b provided in the inner peripheral surface of the valve case 27 are set such that the flow paths 52a and 52b can communicate with the same number of through-holes. In the present embodiment, the length of the flow path 52a provided in the inner peripheral surface of the valve case 27 is set such that the flow path 52a can supply the first resin to half (ten in the present embodiment) of the total number of the through-holes 41a to 41j and 42a to 42j. Likewise, the length of the flow path 52b provided in the inner peripheral surface of the valve case 27 is set such that the flow path 52b can supply the second resin to half (ten in the present embodiment) of the total number of the through-holes 43a to 43j and 44a to 44j. As shown in FIG. 19, the rotational positions of the respective through-holes and the flow paths 52a and 52b about the axis $AX_2$ are set such that the flow path 52b for the second resin communicates with each of the through-holes 43a to 43j while the flow path 52a for the first resin communicates with each of the through-holes 41a to 41j.

Although details will be described later, when the valve body 26 is rotated about the axis $AX_2$, the positional relationship between the flow path 52a and the through-holes 41a to 41j and 42a to 42j changes. As described above, the through-holes 41a to 41j are connected to the resin discharge path, and the through-holes 42a to 42j are connected to the resin supply path to the die 1. Therefore, when the positional relationship between the flow path 52a and the through-holes 41a to 41j and 42a to 42j changes, the ratio of the number of the through-holes, among the through-holes communicating with the flow path 52a, which are connected to the resin discharge path to the number of the through-holes which are connected to the resin supply path changes although the number of the through-holes communicating with the flow path 52a does not change. That is, by rotating the valve body 26, the distribution ratio of the first resin to be discharged to the outside to the first resin to be supplied to the resin supply path to the die 1 can be changed. In the present embodiment, the number of the through-holes to which the flow path 52a can supply the first resin at the same time, the number of the through-holes 41a to 41j connected to the resin discharge path, and the number of the through-holes 42a to 42j connected to the resin supply path are all 10. Therefore, the distribution ratio of the first resin to be discharged to the outside to the first resin to be supplied to the resin supply path to the die can be controlled in 11 levels within the range from 0:10 to 10:0.

In the present embodiment, since the through-holes 43a to 43j and 44a to 44j are provided in the same valve body 26, when the valve body 26 is rotated about the axis $AX_2$, the positional relationship between the flow path 52b and the through-holes 43a to 43j and 44a to 44j also changes at the same time. As described above, the through-holes 43a to 43j are connected to the resin supply path to the die, and the through-holes 44a to 44j are connected to the resin discharge path. Therefore, when the positional relationship between the flow path 52b and the through-holes 43a to 43j and 44a to 44j changes, the ratio of the number of the through-holes, among the through-holes communicating with the flow path 52b, which are connected to the resin supply path to the number of the through-holes which are connected to the resin discharge path changes although the number of the through-holes communicating with the flow path 52b does not change. That is, by rotating the valve body 26, the distribution ratio of the second resin to be supplied to the resin supply path to the die to the second resin to be discharged to the outside can be changed. In the present embodiment, the number of the through-holes to which the flow path 52b can supply the second resin at the same time, the number of the through-holes 43a to 43j connected to the resin supply path, and the number of the through-holes 44a to 44j connected to the resin discharge path are all 10. Therefore, the distribution ratio of the second resin to be supplied to the resin supply path to the die to the second resin to be discharged to the outside can be controlled in 11 levels within the range from 10:0 to 0:10 in synchronization with the distribution of the first resin described above.

In the present embodiment, the first valve for distributing the first resin to the resin supply path and the resin discharge path is composed of a portion of the valve body 26 in which the through-holes 41a to 41j and 42a to 42j are provided and a portion of the valve case 27 in which the flow path 52a is provided. Meanwhile, the second valve for distributing the second resin to the resin supply path and the resin discharge path is composed of another portion of the valve body 26 in which the through-holes 43a to 43j and 44a to 44j are provided and another portion of the valve case 27 in which the flow path 52b is provided. Thus, when both the first valve and the second valve are composed of the same valve body 26 and the same valve case 27, the distribution ratio in the first valve and the distribution ratio in the second valve can be synchronously changed by rotation of the valve body 26 about one axis $AX_2$, whereby the mixing ratio of the first resin to the second resin can be easily controlled.

Operation of Mixing Valve

Figure 20:
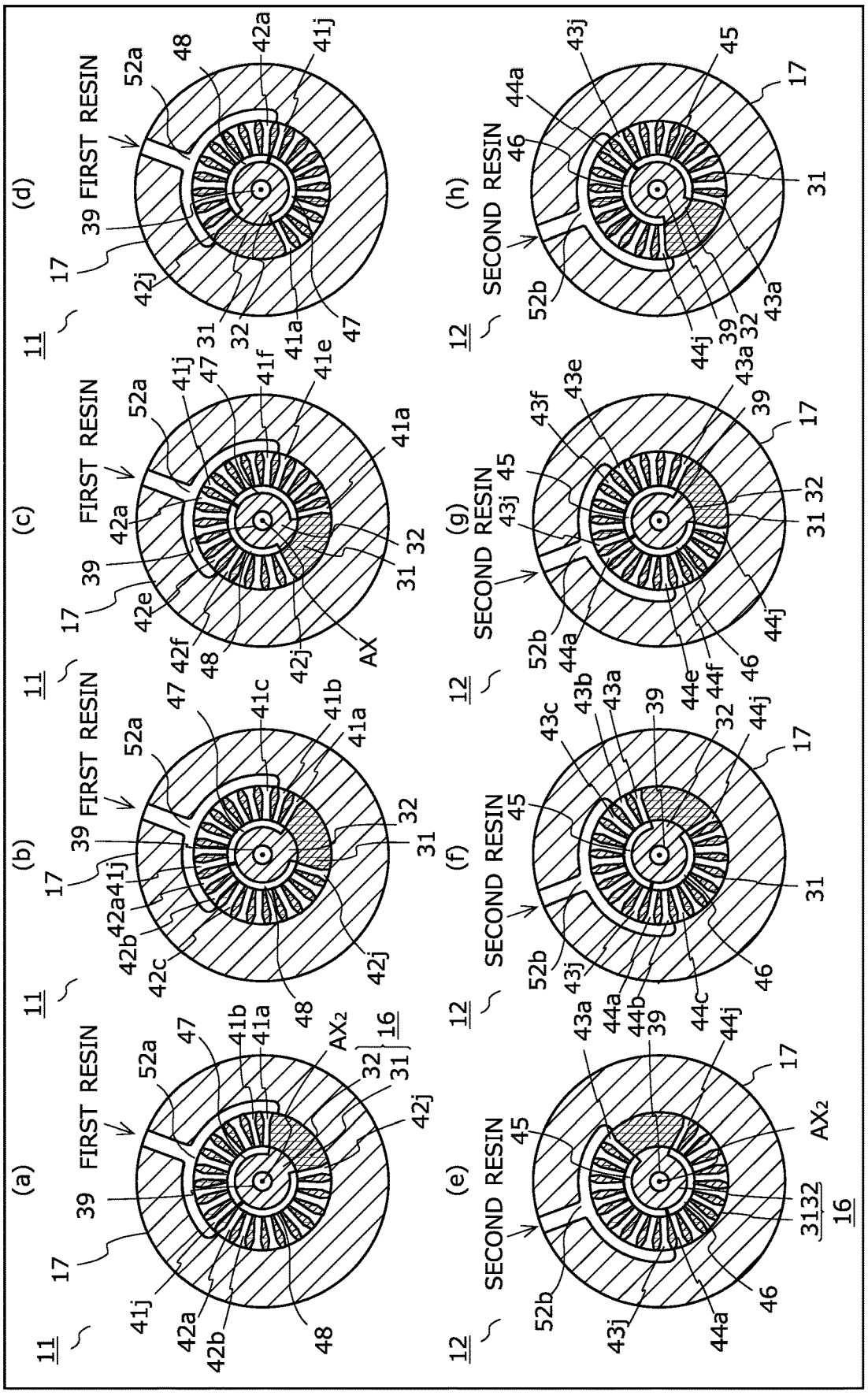
FIG. 20 shows diagrams for describing a method of adjusting a resin mixing ratio by using the mixing valve shown in FIG. 19.

FIG. 20 shows diagrams for describing a method of adjusting the resin mixing ratio by using the mixing valve shown in FIG. 19. In FIG. 20, (a) to (d) each show a cross section corresponding to a position along a line C-C' shown in FIG. 11, and (e) to (h) each show a cross section corresponding to a position along a line D-D' shown in FIG. 11. For convenience in drawing, reference characters of the through-holes are omitted as appropriate. However, in each of (a) to (h) of FIG. 20, the through-holes 41a to 41j and 42a to 42j are arranged in the counterclockwise direction about the axis $AX_2$. In FIG. 10, portions having the same hatching pattern represent the same members, and reference characters thereof are not indicated as appropriate.

State 2-1

First, (a) of FIG. 20 shows a state where the flow path 52a for the first resin communicates with all of the through-holes 41a to 41j of the first cylinder 61. In this state, the first resin supplied from the first extruder through the flow path 52a flows from the through-holes 41a to 41j of the first cylinder 61 to the groove 47 of the second cylinder 62, and is discharged to the outside of the mixing valve 30 through the through-hole 36a and the discharge groove 35 of the first cylinder 61 (see FIG. 12) without being supplied to the die 1.

In this state, as shown in (e) of FIG. 20, the flow path 52b for the second resin communicates with all of the through-holes 43a to 43j of the first cylinder 61. Therefore, all of the second resin supplied from the second extruder through the flow path 52b flows from the through-holes 43a to 43j of the first cylinder 61 to the groove 45 of the second cylinder 62, and is supplied to the die 1 through the flow-in path 40b and the long hole 39 of the second cylinder 62 (see FIG. 16 to FIG. 18).

That is, when the valve body 26 is at the rotational position shown in (a) and (e) of FIG. 20, all of the first resin is discharged while all of the second resin is supplied to the die 1, whereby the mixing ratio of the first resin to the second resin is 0:10.

State 2-2

Next, (b) of FIG. 20 shows a state where the valve body 26 is rotated, from the state shown in (a) of FIG. 20, in the clockwise direction about the axis $AX_2$ by an angle corresponding to two through-holes. As described above, the flow path 52a has a length that allows the flow path 52a to communicate with ten through-holes that are consecutive in the circumferential direction. Therefore, when the valve body 26 is rotated by an angle corresponding to two through-holes, communication of the flow path 52a with the two through-holes 41a and 41b at the most counterclockwise side is canceled, and the eight through-holes 41c to 41j of the first cylinder 61 and the two through-holes 42a and 42b consecutive thereto communicate with the flow path 52a for the first resin.

In this state, a portion, of the first resin supplied from the first extruder through the flow path 52a, that has been supplied to the through-holes 41c to 41j of the first cylinder 61 (⁸⁄₁₀ of the supplied first resin) flows to the groove 47 of the second cylinder 62, and then is discharged to the outside of the mixing valve 30. Meanwhile, the other portion of the first resin that has been supplied to the through-holes 42a and 42b (²⁄₁₀ of the supplied first resin) flows to the groove 48 of the second cylinder 62 and then flows into the long hole 39 through the flow-in path 40a.

At this time, the rotational position of the valve body 26 relative to the flow path 52b for the second resin is also shifted by the angle corresponding to two through-holes. Therefore, as shown in (f) of FIG. 20, the flow path 52b for the second resin communicates with the eight through-holes 43c to 43j of the first cylinder 61 and with the two through-holes 44a and 44b consecutive thereto. A portion, of the second resin supplied from the second extruder through the flow path 52b, that has been supplied to the through-holes 43c to 43j of the first cylinder 61 (⁸⁄₁₀ of the supplied second resin) flows from the through-holes 43c to 43j of the first cylinder 61 to the groove 45 of the second cylinder 62, and is supplied into the long hole 39 through the flow-in path 40b of the second cylinder. Meanwhile, the other portion, of the second resin supplied from the flow path 52b, that has been supplied to the through-holes 44a and 44b of the first cylinder 61 (²⁄₁₀ of the supplied second resin) flows to the groove 46 of the second cylinder 62, and is discharged to the outside of the mixing valve 30 through the through-hole 36b and the discharge groove 35 of the first cylinder 61.

That is, when the valve body 26 is at the rotational position shown in (b) and (f) of FIG. 20, the first resin supplied to two of the ten through-holes communicating with the flow path 52a and the second resin supplied to eight of the ten through-holes communicating with the flow path 52b are supplied into the long hole 39 of the second cylinder 62, and are mixed with each other in the long hole 39 to be supplied to the die 1. The other portions of the supplied resins are discharged to the outside. Therefore, when the valve body 26 is at the rotational position shown in (b) and (f) of FIG. 20, the mixing ratio of the first resin to the second resin is 2:8.

State 2-3

Next, (c) of FIG. 20 shows a state where the valve body 26 is rotated, from the state shown in (b) of FIG. 20, in the clockwise direction about the axis $AX_2$ by an angle corresponding to three through-holes. As described above, the flow path 52a has a length that allows the flow path 52a to communicate with ten through-holes that are consecutive in the circumferential direction. Therefore, when the valve body 26 is rotated by the angle corresponding to three through-holes, communication of the flow path 52a with the three through-holes 41c to 41e is canceled, and the five through-holes 41f to 41j of the first cylinder 61 and the five through-holes 42a to 42e consecutive thereto communicate with the flow path 52a for the first resin.

In this state, a portion, of the first resin supplied from the first extruder through the flow path 52a, that has been supplied to the through-holes 41f to 41j of the first cylinder 61 (5/10 of the supplied first resin) flows to the groove 47 of the second cylinder 62, and thereafter is discharged to the outside of the mixing valve 30. Meanwhile, the other portion of the first resin that has been supplied to the through-holes 42a to 42e (⁵⁄₁₀ of the supplied first resin) flows to the groove 48 of the second cylinder 62 and then flows into the long hole 39 through the flow-in path 40a.

At this time, the rotation position of the valve body 26 relative to the flow path 52b for the second resin is also shifted by the angle corresponding to three through-holes. Therefore, in the state where the flow path 52a for the first resin communicates with the through-holes 41f to 41j of the first cylinder 61 and with the five through-holes 42a to 42e consecutive thereto, as shown in (g) of FIG. 20, the flow path 52b for the second resin communicates with the five through-holes 43f to 43j of the first cylinder 61 and with the five through-holes 44a to 44e consecutive thereto. A portion, of the second resin supplied from the second extruder through the flow path 52b, that has been supplied to the through-holes 43f to 43j of the first cylinder 61 (5/10 of the supplied second resin) flows from the through-holes 43f to 43j of the first cylinder 61 to the groove 45 of the second cylinder 62, and is supplied into the long hole 39 through the flow-in path 40b of the second cylinder. The other portion, of the second resin supplied from the flow path 52b, that has been supplied to the through-holes 44a to 44e of the first cylinder 61 (5/10 of the supplied second resin) flows to the groove 46 of the second cylinder 62, and is discharged to the outside of the mixing valve 30 through the through-hole 36b and the discharge groove 35 of the first cylinder 61.

That is, when the valve body 26 is at the rotational position shown in (c) and (g) of FIG. 20, the first resin supplied to five of the ten through-holes communicating with the flow path 52a and the second resin supplied to five of the ten through-holes communicating with the flow path 52b are supplied to the long hole 39 of the second cylinder 62, and are mixed with each other in the long hole 39 to be supplied to the die 1. The other portions of the supplied resins are discharged to the outside. Therefore, when the valve body 26 is at the rotational position shown in (c) and (g) of FIG. 20, the mixing ratio of the first resin to the second resin is 5:5.

State 2-4

Next, (d) of FIG. 20 shows a state where the valve body 26 is rotated, from the state shown in (c) of FIG. 20, in the clockwise direction about the axis $AX_2$ by an angle corresponding to five through-holes. As described above, the flow path 52a has a length that allows the flow path 52a to communicate with ten through-holes that are consecutive in the circumferential direction. Therefore, when the valve body 26 is rotated by the angle corresponding to five through-holes, communication of the flow path 52a with the through-holes 41f to 41j is canceled, and all of the ten through-holes 42a to 42j at the most counterclockwise side communicate with the flow path 52a for the first resin. In this state, the first resin supplied from the first extruder through the flow path 52a flows from the through-holes 42a to 42j of the first cylinder 61 to the groove 48 of the second cylinder 62, and then flows into the long hole 39 through the flow-in path 40a of the second cylinder 62.

In this state, as shown in (h) of FIG. 20, the flow path 52b for the second resin communicates with all of the through-holes 44a to 44j of the first cylinder 61. Therefore, all of the second resin supplied from the second extruder through the flow path 52a flows from the through-holes 44a to 44j of the first cylinder 61 to the groove 46 of the second cylinder 62, and is discharged to the outside of the mixing valve 3 through the through-hole 36b and the discharge groove 35 of the first cylinder 61.

Therefore, when the valve body 26 is at the rotational position shown in (d) and (h) of FIG. 20, all of the first resin is supplied to the die 1 while all of the second resin is discharged, whereby the mixing ratio of the first resin to the second resin is 10:0.

In FIG. 20, the examples in which the mixing ratio of the first resin to the second resin is varied to be 0:10, 2:8, 5:5, and 10:0 have been representatively described. However, the first resin and the second resin can also be mixed at any mixing ratio ranging from 0:10 to 10:0, depending on the rotational position of the valve body 26. In addition, the mixing ratio can be adjusted within a desired range by increasing/decreasing the number of through-holes as appropriate.

As described above, in the flexible tube production apparatus 200 according to the present embodiment, the ratio of the number a of the through-holes communicating with the resin discharge path, among the through-holes communicating with the flow path 52a for the first resin, to the number b of the through-holes communicating with the resin supply path (long hole 39) for supplying the resin to the die 1 is equal to the ratio of the number c of the through-holes communicating with the resin supply path (long hole 39) for supplying the resin to the die 1, among the through-holes communicating with the flow path 52b for the second resin, to the number d of the through-holes communicating with the resin discharge path (a, b, c, d: integers not smaller than 0). In other words, regardless of the rotation angle of the valve body 26, the number of the through-holes used for supply of the first resin is always equal to the number of the through-holes used for discharge of the second resin, and the number of the through-holes used for discharge of the first resin is always equal to the number of the through-holes used for supply of the second resin. Since the number of the through-holes communicating with the flow path 52a for the first resin is equal to the number of the through-holes communicating with the flow path 52b for the second resin, the number of the through-holes communicating with the resin supply path (long hole 39), i.e., the sum of the number b of the through-holes and the number c of the through-holes, is constant.

Since the flexible tube production apparatus 200 is configured as described above, if the distribution ratios of the first resin and the second resin are changed depending on the rotation angle of the valve body 26, the supply amount of the second resin to the long hole 39 decreases as the supply amount of the first resin to the long hole 39 increases. Thus, the mixing ratio of the first resin to the second resin can be changed. Therefore, in the flexible tube production apparatus 200 according to the present embodiment, the mixing ratio of the first resin to the second resin in the die 1 can be changed while the total of the amount of the first resin to be supplied from the first valve 11 to the die 1 and the amount of the second resin to be supplied from the second valve 12 to the die 1 is kept constant in the mixing valve 3. When the resin layer (outer layer tube) of the flexible tube is extrusion-molded with the valve bodies 16 of the first valve 11 and the second valve 12 being rotated, the mixing ratio of the first resin to the second resin, which form the resin layer, can be continuously changed. For example, if resins having different hardnesses are used as the first resin and the second resin, the hardness of the resin layer can be gradually increased or decreased from one end to the other end of the catheter shaft. Therefore, with the flexible tube production apparatus 200 according to the present embodiment, it is possible to produce a catheter shaft in which the property of the resin layer, such as the hardness, is naturally changed along the length direction thereof, in contrast to the conventional production method.

Third Embodiment

Configuration of Flexible Tube Production Apparatus

Figure 21:
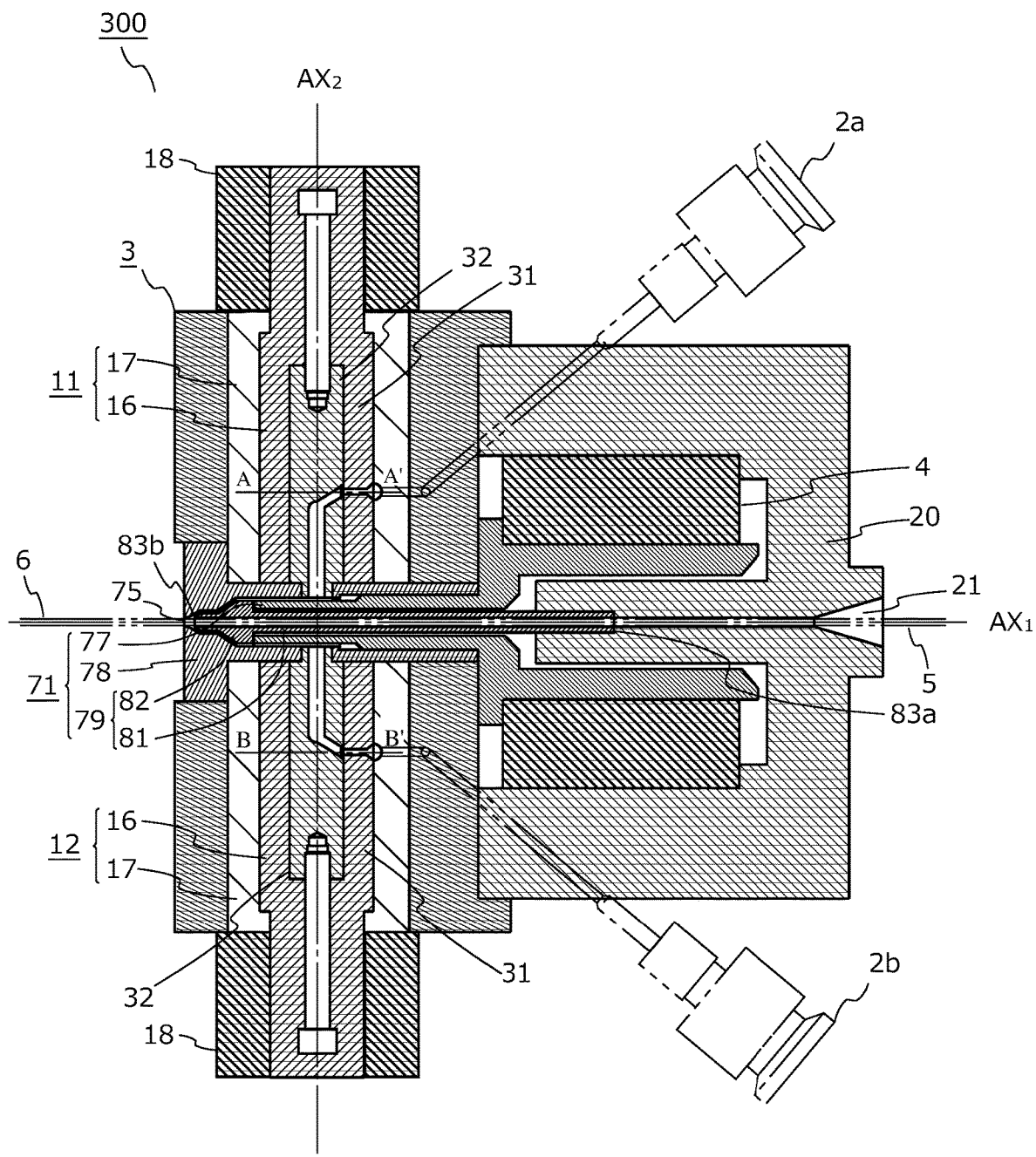
FIG. 21 is a horizontal cross-sectional view showing the schematic configuration of a flexible tube production apparatus according to a third embodiment.
Figure 22:
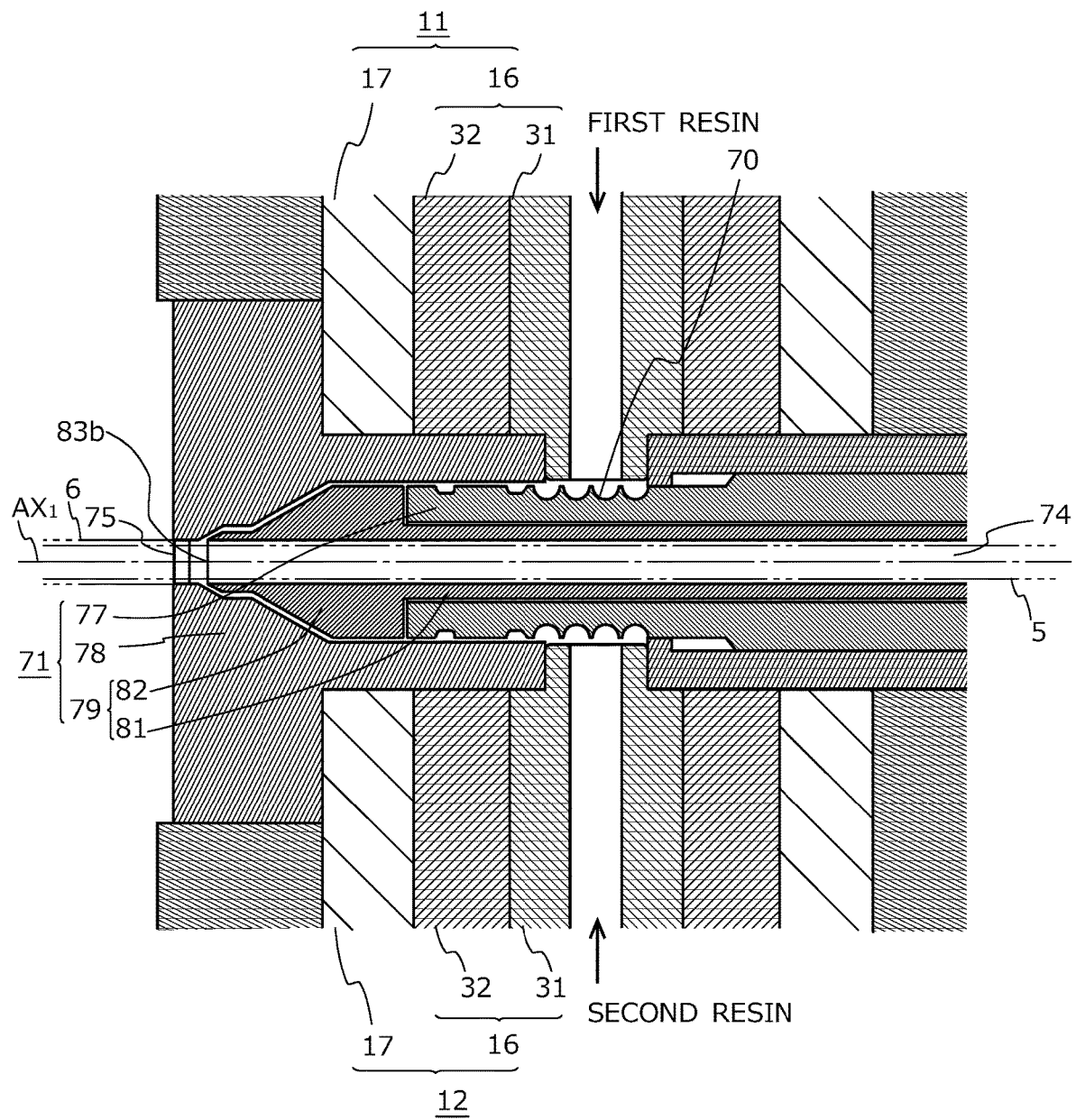
FIG. 22 is an enlarged view of a tip portion of a die shown in FIG. 21.

FIG. 21 is a horizontal cross-sectional view showing a schematic configuration of a flexible tube production apparatus according to a third embodiment. FIG. 22 is an enlarged view of a tip portion of the die shown in FIG. 21.

The flexible tube production apparatus 300 includes a die 71, a first extruder 2a, a second extruder 2b, a mixing valve 3, and a motor 4. The flexible tube production apparatus 300 is fixed to a predetermined mounting base or the like with a pedestal interposed therebetween. Although not shown, a supply device for supplying a blade wire 5, a haul-off device for hauling off a flexible tube 6 that has been extrusion-molded, and the like are provided as appropriate at the upstream side and the downstream side of the flexible tube production apparatus 300. The blade wire 5 is conveyed from the rear side to the front side of the flexible tube production apparatus 300 in the leftward direction shown in FIG. 21 and FIG. 22. The blade wire 5 is obtained by providing a blade (net tube) on an inner layer tube, and inserting a core wire (guide wire) into a hollow part of the inner layer tube. The flexible tube 6 is obtained by providing an outer layer tube at the surface of the blade wire 5. A catheter shaft is obtained by extracting the core wire of the blade wire after molding of the outer layer tube.

The die 71 is a die for extruding a resin onto the outer face of the blade wire 5, and has an inner die 77, an outer die 78, and a tubular member 79. The inner die 77, the outer die 78, and the tubular member 79 are disposed such that the center axes thereof are coaxial with each other. Hereinafter, the center axis common to the inner die 77, the outer die 78, and the tubular member 79 is referred to as an axis $AX_1$.

The tubular member 79 is a tubular member having a through-hole 74 that allows the blade wire 5 to be inserted from a rear end 83a to a front end 83b. The rear end 83a is an open end for insertion of the blade wire 5, and the front end 83b is an open end for feeding-out of the blade wire 5. The tubular member 79 includes a tubular first member 81 having the rear end 83a, and a tubular second member 82 that is connected to the first member 81 and has the front end 83b. The first member 81 and the second member 82 may be integrally formed of the same material, or may be obtained by combining separately formed members. The outer diameter of the first member 81 is substantially constant. The first member 81 is housed in the inner die 77 described later while penetrating the inner die 77. The outermost diameter of the second member 82 is greater than the outer diameter of the first member 81. In the present embodiment, the second member 82 has a tapered shape in which the outer diameter thereof decreases from a connecting part with the first member 81 toward the front end 83b. Further, the second member 82 has a columnar surface with the outer diameter thereof being substantially constant, in a portion thereof within a predetermined range from the connecting part with the first member 81 in the axis $AX_1$ direction. A portion, of the tubular member 79, within a predetermined range from the rear end 83a is fixed to the housing 20, whereby rotation of the tubular member 79 about the axis $AX_1$ is regulated.

The housing 20 to which the tubular member 79 is fixed is provided with a through-hole 21 that is coaxial with the axis $AX_1$ and is continuous to the through-hole 74 of the tubular member 79. The through-hole 21 of the housing 20, the through-hole 74 of the tubular member 79, and the extrusion hole 75 of the outer die 78 form a path that allows the blade wire 5 to pass through.

The inner die 77 is a cylindrical member having a through-hole extending along the axis $AX_1$. The first member 81 of the tubular member 79 described above is inserted into the through-hole of the inner die 77. The inner die 77 surrounds the outer peripheral surface of the first member 81, and is adjacent in the axis $AX_1$ direction to the second member 82 of the tubular member 79. The outer peripheral surface of the first member 81 of the tubular member 79 and the inner peripheral surface of the through-hole of the inner die 77 are sliding surfaces that are mutually slidable. In addition, an end face of the inner die 77 on the front end 83b side and an end face of the second member 82 on the rear end 83a side are sliding surfaces that are mutually slidable. That is, the inner die 77 is rotatably supported about the axis $AX_1$ by the tubular member 79 fixed to the housing 20. A helically extending groove 70 is formed at the outer face of the inner die 77. The groove 70 is provided for kneading the resin supplied to a resin flow path provided between the inner die 77 and the outer die 78. In the present embodiment, as shown in FIG. 22, a portion, of the inner die 77, within a predetermined range from the end face thereof on the front end 83b side and a portion, of the second member 82 of the tubular member 79, within a predetermined range from the end face thereof on the rear end 83a have substantially the same outer diameter.

The outer die 78 is a member having a hollow part corresponding to the outer shapes of the inner die 77 and the second member 82 of the tubular member 79. An extrusion hole 75 for extruding the resin toward the outer face of the blade wire 5 that is fed frontward is provided at the front end of the outer die 78. In the hollow part of the outer die 78, the second member 82 of the tubular member 79 and the inner die 77 are housed adjacently to each other in this order from the extrusion hole 75 side, and a predetermined gap is formed between the outer face of the second member 82 and the inner face of the outer die 78, and between the outer face of the inner die 77 and the inner face of the outer die 78. This gap functions as a resin flow path that introduces the resin discharged from the mixing valve 3 to the extrusion hole 75.

Each of the first extruder 2a and the second extruder 2b is, for example, a screw extruder that melts pellets of the resin and extrudes the resin at a constant speed from an outlet provided at a tip end thereof. The first resin and the second resin are supplied to the first extruder 2a and the second extruder 2b, respectively. The first resin and the second resin are different in at least one of properties such as hardness, tensile strength, elongation, elastic modulus in tension, and bending strength. The melted resins ejected from the first extruder 2a and the second extruder 2b are supplied to the mixing valve 3 described later, mixed at a predetermined mixing ratio in the mixing valve 3, and then supplied to the die 71.

The mixing valve 3 is a member capable of changing the mixing ratio of the two kinds of resins extruded from the first extruder 2a and the second extruder 2b. Since the mixing valve 3 according to the present embodiment is identical to that described in the first embodiment, repeated description is not necessary.

The first extruder 2a, the second extruder 2b, and the mixing valve 3 described above form a resin supply portion capable of supplying the first resin and the second resin to the die 71.

The motor 4 is connected to the inner die 77 of the die 71, and rotates the inner die 77 about the axis $AX_1$ in accordance with control of a control device (not shown).

During extrusion molding of the flexible tube 6, the blade wire 5 inserted from the through-hole 21 of the housing 20 passes the through-hole 74 of the tubular member 79 and is pulled out from the extrusion hole 75 of the outer die 78 to the front of the flexible tube production apparatus 300, as shown by a two-dot chain line in FIG. 21 and FIG. 22. The blade wire 5 pulled out from the extrusion hole 75 of the outer die 78 is hauled by a haul-off device (not shown) to be continuously conveyed in the leftward direction in FIG. 21 and FIG. 22. With the blade wire 5 being conveyed, the first resin ejected from the first extruder 2a and/or the second resin ejected from the second extruder 2b are supplied to the resin flow path of the die 71 via the mixing valve 3. Then, the resins are extruded onto the outer face of the blade wire 5 passing through the extrusion hole 75, whereby the blade wire 5 is covered with the resin layer (outer layer tube), resulting in the flexible tube 6.

In the flexible tube production apparatus 300 according to the present invention, supply of the resins to the die 71 is performed while the inner die 77 is being rotated about the axis $AX_1$ by the motor 4. Since the helical groove 70 is formed at the outer face of the inner die 77, the resins supplied to the resin flow path between the outer face of the inner die 77 and the inner face of the outer die 78 are extruded toward the extrusion hole 75 while being kneaded in accordance with rotation of the inner die 77 about the axis $AX_1$. Therefore, the two kinds of resins supplied to the die 71 are actively uniformized through the path from the supply points (the outlets of the first valve 11 and the second valve 12) to the contact position between the inner die 77 and the second member 82 of the tubular member 79. When a flexible tube in which the property (e.g., hardness) of a resin layer is gradually changed along the longitudinal direction thereof is formed by extrusion molding, the mixing ratio of two kinds of resins needs to be changed along with the extrusion. In the flexible tube production apparatus 300 according to the present invention, since rotation of the inner die 77 causes the two kinds of resins to be kneaded in the resin flow path, uneven mixture of the two kinds of resins is hindered, and the property of the resin layer can be continuously and smoothly changed along the longitudinal direction of the flexible tube 6.

In the present embodiment, both extrusion of the resins and kneading of the resins can be performed in the die 71. Therefore, the length and volume of the flow path from the mixing position of the two kinds of resins (in this embodiment, the most upstream portion of the resin flow path provided in the die 71) to the extrusion hole 75 can be reduced as compared with a case where a mixing screw or the like for resin kneading is provided in addition to the die for resin extrusion. Therefore, it is possible to improve a response from when the mixing ratio of the two kinds of resins is switched in the mixing valve 3 to when the mixing ratio of the resins extruded from the extrusion hole 75 is actually changed. Further, it is possible to adjust the length of the portion in which the mixing ratio of the resins changes. Moreover, since the volume of the resin flow path in the die 71 can be reduced, the amount of resin to be discarded during a period from when one flexible tube is produced to when a next flexible tube is produced can be reduced.

The outer layer of the blade wire 5 is formed of a braided layer or a wound layer of a metal wire or an element wire such as resin fiber. As for the element wire, a fine element wire having a diameter less than 1 mm is used. In a general extrusion molding apparatus for a flexible tube, in order to prevent the outer layer of the blade wire 5 from being damaged, the inner die through which the blade wire 5 is inserted is used in its fixed state. In the flexible tube production apparatus 300 according to the present invention, in order to rotate the inner die 77, the tubular member 79 is fixed inside the inner die 77, and the blade wire 5 is inserted so as to pass through the through-hole 74 of the tubular member 79. That is, the die housed inside the outer die 78 is formed to have a double tube structure including the inner die 77 and the tubular member 79. Since rotation of the tubular member 79 about the axis $AX_1$ is inhibited, the blade wire 5 is prevented from being damaged even when the inner die 77 is rotated.

However, in a case where a resin is extrusion-molded on the blade wire 5 while rotating the inner die by a general extrusion molding apparatus that does not have the tubular member according to the present embodiment, the resin is extruded from the extrusion hole while being rotated with the rotation of the inner die. Therefore, depending on the hardness or fluidity of the adopted resin, the resin extruded onto the surface of the blade wire 5 may form a helical extrusion impression. In the present embodiment, the second member 82 of the tubular member 79, which is fixed to the housing 20 and does not rotate, is disposed on the extrusion hole 75 side in the outer die 78. Therefore, even if the resin, which is kneaded as the inner die 77 rotates, is rotated with the rotation of the inner die 77, this rotation is regulated when the resin passes through the flow path between the fixed second member 82 and the outer die 78, whereby the flow of the resin is straightened. Since the rotation of the resin to be extruded from the extrusion hole 75 onto the surface of the blade wire 5 is reduced, the outer diameter of the extrusion-molded flexible tube 6 can be made uniform.

Therefore, according to the present embodiment, it is possible to realize the flexible tube production apparatus 300 suitable for producing a flexible tube in which the mixing ratio of two kinds of resins that form a resin layer is continuously changed. The flexible tube production apparatus 300 according to the present embodiment can be used for producing various flexible tubes having resin layers at their outermost faces. In particular, the flexible tube production apparatus 300 is suitable for producing flexible tubes, such as catheters and endoscope tubes, in which uniformity of resins in a portion where the mixing ratio of the resins changes, accuracy of the change in the mixing ratio of the resins, and dimensional stability are all important.

Similar to the description provided for the first embodiment, the aforementioned die 71 is characterized in that the die 71 can reduce pressure variations in the first-resin flow path from the first extruder 2a to the die 71 and in the second-resin flow path from the second extruder 2b to the die 71, thereby improving accuracy of the rate of change in the mixing ratio of the two kinds of resins that form the resin layer (outer layer tube) and accuracy of the outer diameter dimension of the resin layer. When the aforementioned die 71 is combined with the mixing valve 3 according to the first or second embodiment, the two kinds of resins supplied to the die 71 can be uniformly kneaded. Therefore, it is possible to improve accuracy of the rate of change in the mixing ratio of the two kinds of resins that form the resin layer (outer layer tube) and accuracy of the outer diameter dimension of the resin layer, and it is possible to continuously and smoothly change the mixing ratio in the resin layer along the longitudinal direction of the flexible tube 6.

Fourth Embodiment

Configuration of Flexible Tube Production Apparatus

Figure 23:
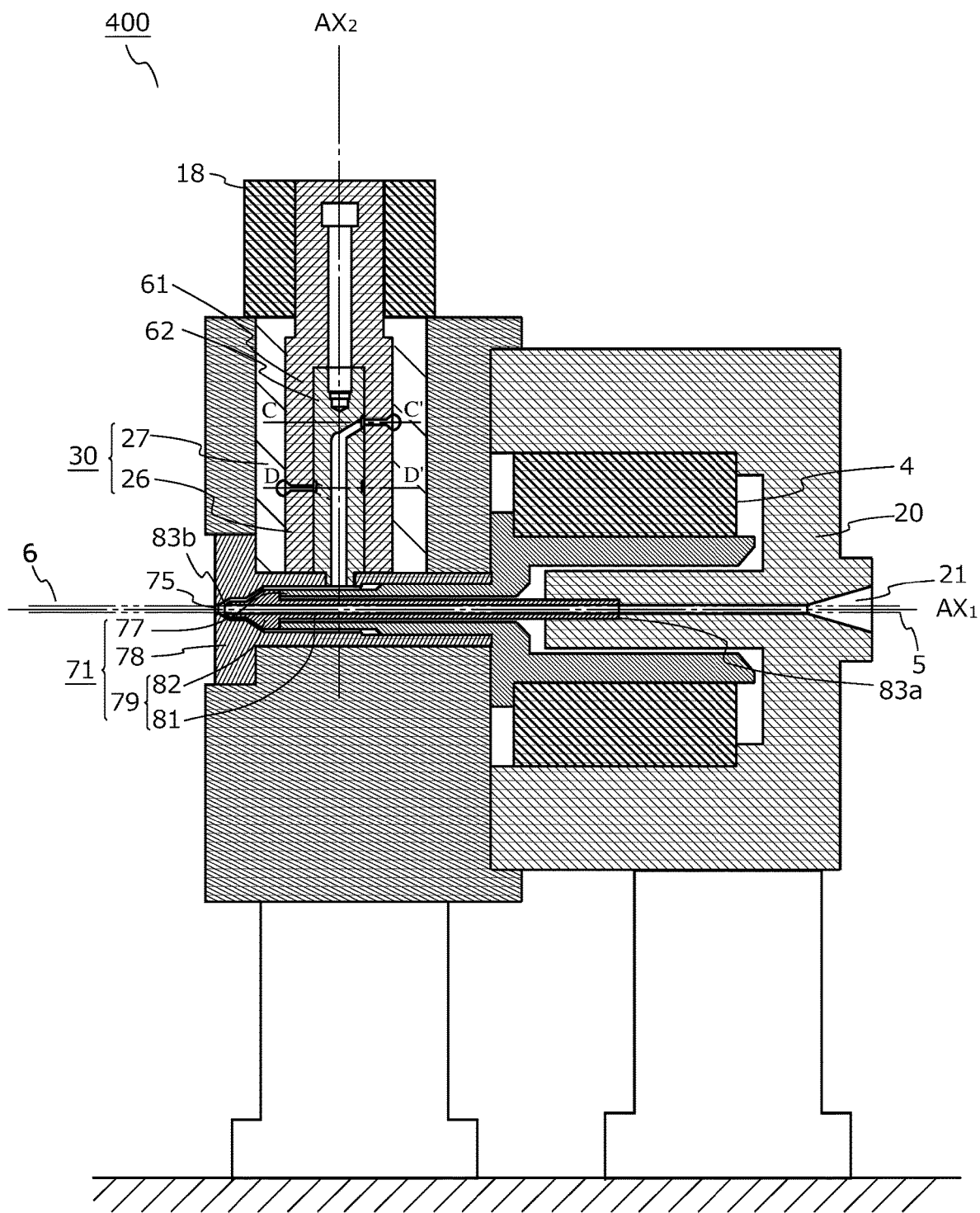
FIG. 23 is a vertical cross-sectional view showing the schematic configuration of a flexible tube production apparatus according to a fourth embodiment.

FIG. 23 is a vertical cross-sectional view showing a schematic configuration of a flexible tube production apparatus according to a fourth embodiment.

The flexible tube production apparatus 400 according to the present embodiment includes a die 71, a first extruder (not shown), a second extruder (not shown), a mixing valve 30, and a motor 4. The mixing valve 30 is supplied with a first resin and a second resin which are different from each other, from the first extruder and the second extruder which are not shown, respectively. The flexible tube production apparatus 400 is fixed to a predetermined mounting base or the like with a pedestal interposed therebetween. Although not shown, in the present embodiment, a supply device for supplying a blade wire 5 to the flexible tube production apparatus 400, a haul-off device for hauling off a flexible tube 6 that has been extrusion-molded, and the like are provided as appropriate at the upstream side and the downstream side of the flexible tube production apparatus 400. Since the mixing valve 30 of the present embodiment is identical to that described in the second embodiment, repeated description is not necessary.

The die 71 included in the flexible tube production apparatus 400 is provided with an inner die 77, an outer die 78, and a tubular member 79 which are similar to those described in the third embodiment. As in the third embodiment, the inner die 77 is rotatably supported by the first member 81 of the tubular member 79, and is rotatable about axis $AX_1$ by the rotation force of the motor 4. Although not shown, as in the third embodiment, a helical groove (not shown) for kneading a melted resin is formed at the outer face of the inner die 77 (see FIG. 22). The outer die 78 surrounds the inner die 77 such that a predetermined gap is formed between the outer die 78 and the outer face of the inner die 77. The outer die 78 has, at a front end thereof, an extrusion hole for extruding the resin. The tubular member 79 is a tubular member having a through-hole through which the blade wire 5 is inserted. As described in the third embodiment, the tubular member 79 includes a tubular first member 81 having an open end for insertion of the blade wire 5, and a tubular second member 82, for feeding-out of the blade wire 5, which is connected to the first member 81. Inside the outer die 78, the first member 81 is housed in the inner die 77, and the second member 82 is disposed adjacent to the inner die 77. As in the third embodiment, the tubular member 79 is fixed to the housing 20 so as to regulate rotation of the tubular member 79 about the axis $AX_1$.

Also, in the present embodiment, during extrusion molding of the flexible tube, supply of the resin to the die 71 is performed while the inner die 77 is rotated about the axis $AX_1$ by the motor 4. Since the helical groove (not shown) is formed at the outer face of the inner die 77, the resin supplied to the resin flow path between the outer face of the inner die 77 and the inner face of the outer die 78 is extruded from the extrusion hole 75 while being kneaded in accordance with rotation of the inner die 77 about the axis $AX_1$. Therefore, with the flexible tube production apparatus 400 according to the present embodiment, when two kinds of resins are mixed and molded into a resin layer of a mixed-resin flexible tube, uniformization of the two kinds of resins can be achieved.

Other Modifications, etc.

In each of the embodiments described above, an example has been described in which the present invention is applied to a catheter shaft production apparatus. However, the configurations of the mixing valve and the production apparatus according to the present invention can also be applied to a production apparatus for a flexible tube having another usage such as a tube for an endoscope.

In each of the embodiments described above, an example has been described in which a catheter shaft is extrusion-molded by using resins having different hardnesses as the two different kinds of resins. However, as the two kinds of resins, resins that are different in any property, not limited to hardness, may be used. For example, if resins having different colors are used as the two kinds of resins, it is also possible to produce an outer layer tube whose color gradually changes from a tip end to an opposite-side portion thereof.

In each of the embodiments described above, the valve case may be divided into a plurality of blocks as appropriate so as to facilitate formation of grooves and flow paths.

In each of the embodiments described above, an example has been described in which 20 through-holes (first openings) for supplying the first resin and 20 through-holes (second openings) for supplying the second resin are provided. However, the number of through-holes is not limited in particular, and may be N (N is a positive integer).

In each of the embodiments described above, an example has been described in which half (10) of the number of the through-holes (first openings) for supplying the first resin are communicated with the resin supply path while the other half (10) thereof are connected to the resin discharge path, and half (10) of the number of the through-holes (second openings) for supplying the second resin are communicated with the resin supply path while the other half (10) thereof are communicated with the resin discharge path. However, the present invention is not limited thereto. In a case where the number of the through-holes (first openings) for supplying the first resin is N (N is a positive integer), m (m is an integer smaller than N) through-holes may be communicated with the resin supply path while the remaining (N-m) through-holes may be communicated with the resin discharge path. In this case, among the N through-holes (second openings) for supplying the second resin, m through-holes may be communicated with the resin discharge path while the remaining (N-m) through-holes may be communicated with the resin supply path. In a case where N is an even number and m is N/2, the number of through-holes communicated with the resin supply path is equal to the number of through-holes communicated with the resin discharge path, and therefore, the resin mixing ratio can be adjusted within a range of 0 to 100%. However, if m is not N/2, the adjustable range of the mixing ratio narrowed, but the mixing ratio can be adjusted within a limited range. For example, in a case where the number of the through-holes for supplying the first resin is 10, the number of the through-holes for discharging the first resin is 5, the number of the through-holes for supplying the second resin is 5, and the number of the through-holes for discharging the second resin is 10, the mixing ratio of the first resin to the second resin is adjustable within a range of 10:0 to 5:5.

In each of the embodiments described above, each supply path provided in the valve case is configured to have a length that allows the supply path to be communicated with half of the number of the through-holes (first openings) for supplying the first resin or half of the number of the through-holes (second openings) for supplying the second resin. However, the present invention is not limited thereto. In a case where the number of the through-holes (first openings) for supplying the first resin to the first cylinder is N (N is a positive integer) while the number of the through-holes (second openings) for supplying the second resin to the first cylinder is also N, the number of through-holes to which the supply path in the valve case can supply the corresponding resin may be less than N.

The flexible tube obtained by the production apparatus according to each of the embodiments described above has a structure in which the surface of the blade is covered with a resin layer, and the resin layer covering the blade is formed of a mixture of two kinds of resins that are different from each other. As described above, with the flexible tube production apparatus according to the present invention, through control of the distribution ratio (ratio of the amount of resin to be supplied to the mixing value to the amount of resin to be discharged) of each of the two kinds of resins, the mixing ratio can be gradually changed. Therefore, the mixing ratio of the two kinds of resins forming the resin layer is changed continuously, not stepwise, from one end to the other end of the flexible tube. Consequently, in the flexible tube obtained by the production apparatus according to the present invention, the hardness can be gradually changed without being suddenly changed in association with a change in the resin ratio.

The present invention can be used as a production apparatus for flexible tubes such as a catheter shaft to be used in producing a medical catheter, and a tube to be used in an endoscope.

As presented above, the embodiments have been described as examples of the technology according to the present disclosure. For this purpose, the accompanying drawings and the detailed description are provided.

Therefore, components in the accompanying drawings and the detailed description may include not only components essential for solving problems, but also components that are provided to illustrate the above described technology and are not essential for solving problems. Therefore, such inessential components should not be readily construed as being essential based on the fact that such inessential components are shown in the accompanying drawings or mentioned in the detailed description.

Further, the above described embodiments have been described to exemplify the technology according to the present disclosure, and therefore, various modifications, replacements, additions, and omissions may be made within the scope of the claims and the scope of the equivalents thereof.

What is claimed is:

1. A flexible tube production apparatus for producing a flexible tube by extrusion molding, comprising:
   a die that kneads a resin and extrudes the resin onto a surface of a blade wire;
   a resin supply portion capable of supplying, to the die, a first resin and a second resin different from the first resin; and
   a motor, wherein
   the die includes
      a cylindrical inner die having an outer face in which a groove is formed, the groove being for kneading the resin,
      a tubular member housed inside the inner die, the tubular member having a through-hole that allows the blade wire to be inserted from one end to the other end of the tubular member, and
      an outer die surrounding the inner die such that a predetermined gap is generated between the outer die and the outer face of the inner die, the outer die having an extrusion hole that extrudes the resins having been supplied to the gap, onto an outer face of the blade wire that is fed from the other end of the tubular member, wherein
   the outer die, the inner die, and the tubular member are arranged such that the center axes thereof are coaxial with each other,
   the tubular member is fixed,
   the resin supply portion supplies the first resin and the second resin to the die while the motor rotates the inner die about the center axis,
   the resin supply portion includes:
      a first extruder that ejects the first resin;
      a second extruder that ejects the second resin; and
      a mixing valve capable of changing a mixing ratio of the first resin ejected from the first extruder to the second resin ejected from the second extruder,
   the mixing valve includes:
      a first valve capable of changing a first distribution ratio that is a ratio of an amount of the first resin to be supplied to the die to an amount of the first resin to be discharged to the outside; and
      a second valve capable of changing a second distribution ratio that is a ratio of an amount of the second resin to be supplied to the die to an amount of the second resin to be discharged to the outside,
   the mixing valve changes the first distribution ratio and the second distribution ratio, with a total of the amount of the first resin to be supplied from the first valve to the die and the amount of the second resin to be supplied from the second valve to the die being kept constant, thereby increasing or decreasing the mixing ratio of the first resin to the second resin in association with the extrusion molding of the flexible tube,
   the first valve includes
      a columnar first valve body that is rotatable about a center axis, and
      a first case that has an inner peripheral surface slidable with an outer peripheral surface of the first valve body, and houses the first valve body within the inner peripheral surface so that the first valve body is slidable and rotatable,
   the second valve includes
      a columnar second valve body that is rotatable about a center axis, and
      a second case that has an inner peripheral surface slidable with an outer peripheral surface of the second valve body, and houses the second valve body within the inner peripheral surface so that the second valve body is slidable and rotatable,
   the first valve body is provided with N first openings that are arranged at equal angles in a circumferential direction on the outer peripheral surface of the first valve body, N being a positive integer,
   the second valve body is provided with N second openings, having the same shape as the first openings, that are arranged at equal angles in a circumferential direction on the outer peripheral surface of the second valve body,
   among the first openings, m first openings continuous in the circumferential direction communicate with a first resin supply path for supplying the first resin to the die, and first openings that remain, upon subtracting the m first openings from the N first openings, and are continuous to the m first openings communicate with a first resin discharge path for discharging the first resin to the outside, m being a positive integer smaller than N, among the second openings, m second openings continuous in the circumferential direction communicate with a second resin discharge path for discharging the second resin to the outside, and second openings that remain, upon subtracting the m second openings from the N second openings, and are continuous to the m second openings communicate with a second resin supply path for supplying the second resin to the die, the first case is provided with a first supply portion capable of supplying the first resin ejected from the first extruder, to n pieces of the first openings, n being a positive integer smaller than N, the second case is provided with a second supply portion capable of supplying the second resin ejected from the second extruder, to n pieces of the second openings, and a sum of the number of first openings communicating with both the first supply portion and the first resin supply path and the number of second openings communicating with both the second supply portion and the second resin supply path, is n.

2. The flexible tube production apparatus according to claim 1, wherein the number of the first openings communicating with the first resin supply path, the number of the first openings communicating with the first resin discharge path, and the number of the first openings to which the first resin is supplied from the first supply portion, are equal to each other, and the number of the second openings communicating with the second resin supply path, the number of the second openings communicating with the second resin discharge path, and the number of the second openings to which the second resin is supplied from the second supply portion, are equal to each other.

\* \* \* \* \*